(12) United States Patent
Wiley, II

(10) Patent No.: US 11,475,986 B2
(45) Date of Patent: Oct. 18, 2022

(54) IDENTIFYING AND PROVIDING AGGREGATED PRESCRIPTION BENEFITS TO CONSUMERS OF PRESCRIPTION PRODUCTS AT THE POINT OF SALE

(71) Applicant: Joseph Lee Wiley, II, West Monroe, LA (US)

(72) Inventor: Joseph Lee Wiley, II, West Monroe, LA (US)

( * ) Notice: Subject to any disclaimer, the term of this patent is extended or adjusted under 35 U.S.C. 154(b) by 114 days.

(21) Appl. No.: 16/444,763

(22) Filed: Jun. 18, 2019

(65) Prior Publication Data

US 2019/0385722 A1 Dec. 19, 2019

Related U.S. Application Data

(60) Provisional application No. 62/686,246, filed on Jun. 18, 2018.

(51) Int. Cl.
*G16H 20/10* (2018.01)
*G06Q 30/06* (2012.01)
*G16H 10/60* (2018.01)

(52) U.S. Cl.
CPC ......... *G16H 20/10* (2018.01); *G06Q 30/0633* (2013.01); *G16H 10/60* (2018.01)

(58) Field of Classification Search
CPC ..... G16H 10/60; G16H 20/10; G06Q 30/0633
See application file for complete search history.

(56) References Cited

U.S. PATENT DOCUMENTS

| | | | |
|---|---|---|---|
| 7,840,424 B2 | 11/2010 | Wiley et al. | |
| 8,065,160 B1 * | 11/2011 | Gatti | G06Q 10/00 705/2 |
| 8,635,083 B1 * | 1/2014 | Casu | G06Q 30/06 705/2 |
| 10,552,579 B1 * | 2/2020 | Chhabra | H04L 63/10 |
| 2005/0240473 A1 * | 10/2005 | Ayers, Jr. | G06Q 30/02 705/14.69 |
| 2006/0116905 A1 * | 6/2006 | Yered | G16H 40/67 705/2 |
| 2007/0162303 A1 * | 7/2007 | Wiley, II | G16H 20/10 705/400 |

(Continued)

*Primary Examiner* — Robert W Morgan
*Assistant Examiner* — Chance L Smith
(74) *Attorney, Agent, or Firm* — Craft Chu PLLC; Andrew W. Chu

(57) ABSTRACT

A computer-implemented method for managing prescription benefits in prescription claim or inquiry requests performed by one or more computers in a prescription order processing system includes receiving a prescription claim request related to a consumer from a requesting entity. A crosswalk file is retrieved that comprises information from a plurality of health plan member files describing benefits available to the consumer provided by a plurality of benefit providers. The crosswalk file is used to automatically determine an order submission sequence indicating an order in which claim or inquiry requests corresponding to the benefits are submitted to the benefit providers. The claim or inquiry requests are submitted to the benefit providers according to the order submission sequence. Responses from the benefit providers are automatically aggregated in order to generate an aggregated response to the prescription claim request. The aggregated response is transmitted to the requesting entity.

6 Claims, 26 Drawing Sheets

(56) References Cited

U.S. PATENT DOCUMENTS

| | | | |
|---|---|---|---|
| 2010/0070298 A1* | 3/2010 | Kalies | G06Q 10/10 |
| | | | 705/2 |
| 2011/0196697 A1* | 8/2011 | Akers | G06Q 40/08 |
| | | | 705/2 |
| 2013/0054261 A1* | 2/2013 | Dufour | G06Q 30/0226 |
| | | | 705/2 |
| 2016/0321410 A1* | 11/2016 | Timmerman | G16H 70/40 |
| 2018/0121621 A1* | 5/2018 | Wiley, II | G06Q 30/0239 |
| 2019/0370845 A1* | 12/2019 | Peysekhman | G06Q 40/08 |

\* cited by examiner

| HP Member ID | Member FN | Member LN | HP Group | HP PCN | HP Bin | HP DOB | HP Gender Code | HP Dependent Code | HP Relationship Code |
|---|---|---|---|---|---|---|---|---|---|
| 8123456789 | John | Doe | Group | ABC | 610233 | 01/01/2001 | 1 | 1 | 01 |

FIG. 2

Health Plan Member File

| HP Member ID | Member FN | Member LN | HP Group | HP PCN | HP BIN | HP DOB | HP Gender Code | HP Dependent Code | HP Relationship Code |
|---|---|---|---|---|---|---|---|---|---|
| 8123456789 | John | Doe | Group | ABC | ABC | 01/01/2001 | 1 | 1 | 01 |

Member ID Generator

- Accepts input of all data elements from health plan member file
- Uses proprietary or conventional algorithm to generate unique multiple digit (e.g., 18 digit) alpha-numeric member identifier
- Assigns the generated (GEN) member identifier to the appropriate GEN BIN, PCN, Group combination
- Adds the generated-GEN member identifier, GEN BIN, PCN, Group, etc., into the health plan member file information and store this as a separate crosswalk database file
- Creates GEN member file to be loaded into the appropriate program design rule set

Member File Notes

- Universal Patient Identifier (UPI) member file may contain an indicator identifying the member as having insurance coverage that does not allow use of prescription coupons or vouchers if it is involved in payment for the prescription claim
- Each of these files are provided for exemplary purposes only. There may be addition fields that are included in the files as well
- The UPI member file is for each program under which the member is subject to coverage
- The UPI crosswalk file may have many AWS member files included within it to create a complete crosswalk that completely identifies the member within each program relative to each other included program

Gen Member File

| GEN Member ID | GEN Group | Member ER FN | Member ER LN | GEN PCN | GEN BIN | GEN DOB | GEN Dependent Code | GEN Relationship Code |
|---|---|---|---|---|---|---|---|---|
| ABC123DEF987654ZYX | DEF | John | Doe | MOB | 610210 | 01/01/2001 | 1 | 01 |

UPI Crosswalk File

| GEN Member ID | HP Member ID | HP Group | HP PCN | HP BIN | HP DOB | HP Dependent Code | HP Relationship Code |
|---|---|---|---|---|---|---|---|
| ABC123DEF987654ZYX | 8123456789 | Group | ABC | ABC | 01/01/2001 | 1 | 01 |

FIG. 3

Description for Figure 4

1.     103 sends claim targeting information to 102

2.     Claim processing information and benefit design information is exchanged a.     103 provides to 104 b.     104 provides to 103

3.     Claim processing information and benefit design information is exchanged a.     103 provides to 106 b.     106 provides to 103

4.     Claim processing information and benefit design information is exchanged a.     103 provides to 107 b.     107 provides to 103

5.     100 or 109 presents prescription order or inquiry to 101

6.     101 sends prescription benefits claim request to 102

7.     102 identifies claim request as meeting requirements provided from 103 in step 1 and redirects claim request to 103

8.     103 determines all possible benefits claims subject to claim request, sets claim order sequence, populates first claim request and submits to 102 to be forwarded to 104

9.     102 forwards claim one to 104 for benefits consideration 10.     104 considers claim for benefits eligibility, approves or denies the request and sends response to 102

11.     102 identifies the response as originating from 103 and forwards response to 103

12.     103 accepts response, records it, extracts data from it, populates second claim request and submits to 102 to be forwarded to 105

13.     102 forwards claim two to 105

14.     105 considers claim for benefits eligibility, approves or denies the request and sends response to 102

FIG. 4B

Description for Figure 4 (Continued)

15. 102 identifies the response as originating from 103 and forwards response to 103

16. 103 accepts response, records it, extracts data from it, populates third claim request and submits to 102 to be forwarded to 106

17. 106 considers claim for benefits eligibility and sends eligible inventory inquiry to 1010

18. 1010 considers the quantity requested in claim three against the eligible inventory of the specific product requested in claim three on record 19. 1010 denies or confirms the presence of sufficient inventory available to the requesting pharmacy to fulfill the request and sends response to 106

20. 105 considers claim for benefits eligibility, approves or denies the request and sends response to 102

21. 102 identifies the response as originating from 103 and forwards response to 103

22. 103 accepts response, records it, extracts data from it, populates fourth claim request and submits to 102 to be forwarded to 107

23. 107 considers claim for benefits eligibility and sends eligible inventory inquiry to 1010

24. 1010 considers the quantity requested in claim four against the eligible inventory of the specific product requested in claim three on record 25. 1010 denies or confirms the presence of sufficient inventory available to the requesting pharmacy to fulfill the request and sends response to 107

26. 107 considers claim for benefits eligibility, approves or denies the request and sends response to 102

27. 102 identifies the response as originating from 103 and forwards response to 103

28. 102 recognizes that no further claims related to claim one need to be generated or submitted to benefits administrators on behalf of the pharmacy, aggregates the responses from all of the benefits administrators creates an aggregated claim response to claim one and forwards to 102 to be returned to 101

29. 102 returns aggregated claim to 101

30. 103 creates a data file containing each of the individual claims that are included in the aggregated response for claim one and sends the file to 101 for documentation and reconciliation purposes.

NOTE: Steps one through twenty-nine take place in a real time environment taking fifteen seconds or less to complete them in total. Step thirty does not take place in real time, rather it could be immediately following the real time transaction or in a scheduled delivery at a later time.

*FIG. 4C*

Description for Figure 5

1. 103 sends claim targeting information to 102

2. Claim processing information and benefit design information is exchanged a. 103 provides to 104 b. 104 provides to 103

3. Claim processing information and benefit design information is exchanged a. 103 provides to 106 b. 106 provides to 103

4. Claim processing information and benefit design information is exchanged a. 103 provides to 107 b. 107 provides to 103

5. 100 or 109 presents prescription order or inquiry to 101

6. 101 sends prescription benefits claim request to 102

7. 102 identifies claim request as meeting requirements provided from 103 in step 1 and redirects claim request to 103

8. 103 determines all possible benefits claims subject to claim request, sets claim order sequence, populates first claim request and submits to 102 to be forwarded to 104

9. 102 forwards claim one to 104 for benefits consideration 10. 104 considers claim for benefits eligibility, approves or denies the request and sends response to 102

11. 102 identifies the response as originating from 103 and forwards response to 103

12. 103 accepts response, records it, extracts data from it, populates second claim request and submits to 102 to be forwarded to 1011

13. 102 forwards claim two to 1011

14. 1011 considers claim for benefits eligibility, approves or denies the request and sends response to 102

15. 102 identifies the response as originating from 103 and forwards response to 103

*FIG. 5B*

Description for Figure 5 (Continued)

16. 103 accepts response, records it, extracts data from it, populates third claim request and submits to 102 to be forwarded to 106

17. 106 considers claim for benefits eligibility and sends eligible inventory inquiry to 1010

18. 1010 considers the quantity requested in claim three against the eligible inventory of the specific product requested in claim three on record 19. 1010 denies or confirms the presence of sufficient inventory available to the requesting pharmacy to fulfill the request and sends response to 106

20. 105 considers claim for benefits eligibility, approves or denies the request and sends response to 102

21. 102 identifies the response as originating from 103 and forwards response to 103

22. 103 accepts response, records it, extracts data from it, populates fourth claim request and submits to 102 to be forwarded to 107

23. 107 considers claim for benefits eligibility and sends eligible inventory inquiry to 1010

24. 1010 considers the quantity requested in claim four against the eligible inventory of the specific product requested in claim three on record 25. 1010 denies or confirms the presence of sufficient inventory available to the requesting pharmacy to fulfill the request and sends response to 107

26. 107 considers claim for benefits eligibility, approves or denies the request and sends response to 102

27. 102 identifies the response as originating from 103 and forwards response to 103

28. 102 recognizes that no further claims related to claim one need to be generated or submitted to benefits administrators on behalf of the pharmacy, aggregates the responses from all of the benefits administrators creates an aggregated claim response to claim one and forwards to 102 to be returned to 101

29. 102 returns aggregated claim to 101

30. 103 creates a data file containing each of the individual claims that are included in the aggregated response for claim one and sends the file to 101 for documentation and reconciliation purposes.

NOTE: Steps one through twenty-nine take place in a real time environment taking fifteen seconds or less to complete them in total. Step thirty does not take place in real time, rather it could be immediately following the real time transaction or in a scheduled delivery at a later time.

FIG. 5C 1. 103 Sends claim targeting information to 102
2. 103 Sends Rebate Program setup information to 1012
3. 103 Sends plan setup information to 1012
4. 103 Sends plan setup information to 1012
5. 100 or 109 presents prescription to 101
6. 101 sends Rx claim request to 102
7. 102 identifies claim and sends to 1012
8. 1012 builds claim request and sends to 102
9. 102 sends claim 1011
10. 1011 adjudicates claim and returns to 102

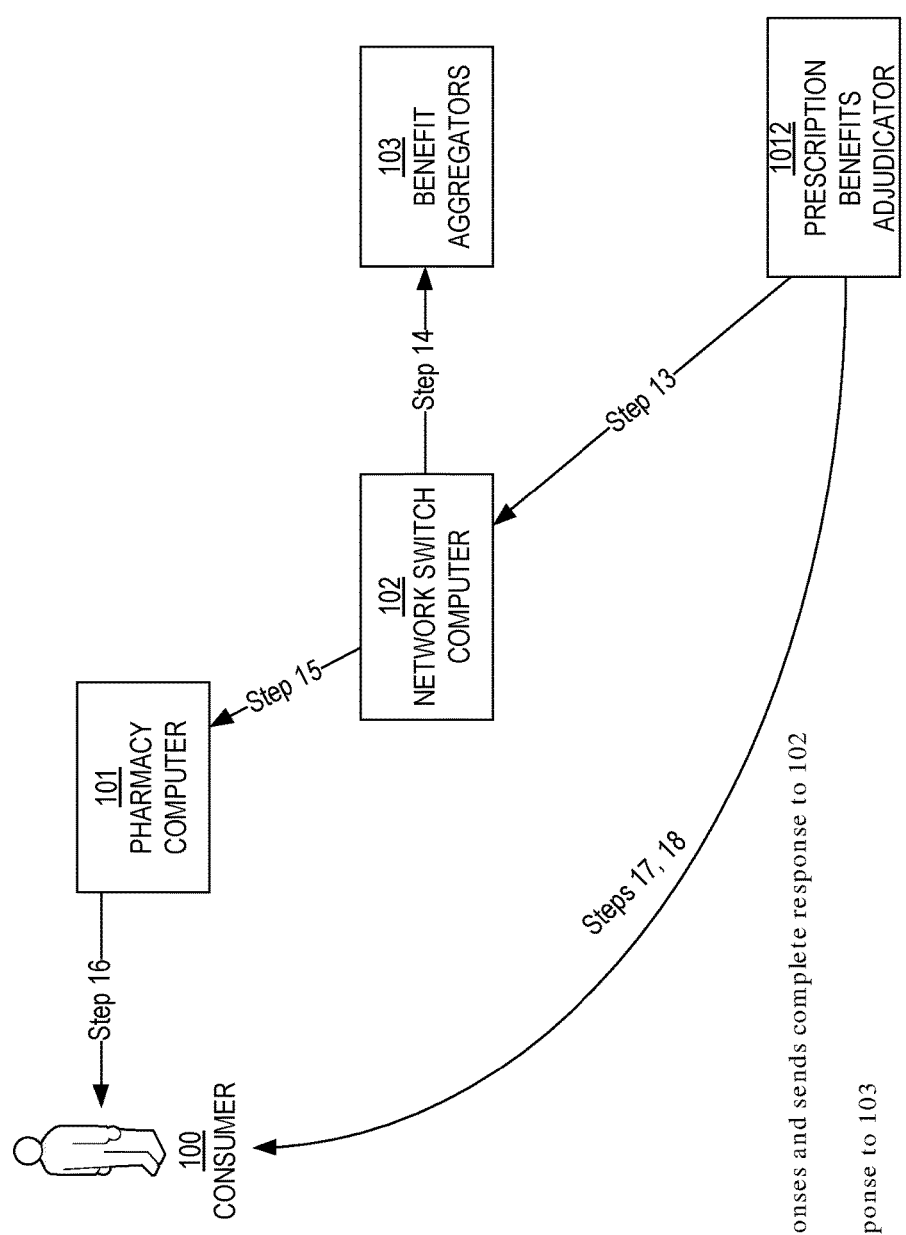

IDENTIFYING AND PROVIDING AGGREGATED PRESCRIPTION BENEFITS TO CONSUMERS OF PRESCRIPTION PRODUCTS AT THE POINT OF SALE

RELATED APPLICATIONS

This application claims the benefit of priority to U.S. Provisional Patent Application Ser. No. 62/686,246, filed on Jun. 18, 2018, the entire contents of which are hereby incorporated by reference herein.

FIELD OF THE INVENTION

The invention relates generally to how financial benefits are identified and provided to consumers during an electronically filed prescription transaction, whether the transaction be an inquiry or formal benefit claim request and whether the consumer be an individual or a business entity.

BACKGROUND

There are many different forms of financial assistance provided by pharmaceutical manufacturers, suppliers, cash discount programs, and insurers that reduce the financial burden of the prescription consumer, whether it is an individual or a business entity. However, there are several barriers that prevent full utilization or access to these funds at the point of sale. In addition to barriers to utilization, there also exists a lack of transparency in the flow of the financial amounts through the various involved entities from the originator to the end recipient. It has been recently exposed that this lack of transparency has resulted in overcharges to various benefit provider, government agencies and the people that receive the prescription treatments.

Pharmaceutical manufacturer coupons are widely available and are relied upon by individual consumers to enable them to afford the out of pocket costs of their needed medication. However, there are barriers to having that assistance available such as: the prescriber doesn't have any of the coupons at the clinic when the consumer obtains the prescription, the consumer forgets to bring the coupon to the pharmacy for use when getting the prescription filled, the consumer utilizes a different pharmacy for some reason and the coupon processing information is not available to the second pharmacy, the coupon has expired and the consumer doesn't have access to the updated coupon, etc. While there are electronic coupons available when the pharmacy utilizes an intelligent network switch, such as described in U.S. Pat. No. 7,840,424, Wiley II, et al.) and those do help, they are not available at any pharmacy that does not utilize the RelayHealth switch. Further, the individual consumer doesn't know what switch the pharmacy they choose to fill their prescriptions utilizes and doesn't choose a pharmacy based on that information. There needs to be a reliable means for access to the coupon benefits no matter what switch or what pharmacy the consumer chooses to fill their prescription.

Pharmaceutical wholesalers and distributors would like to offer a consumer discount or prescription coupon at the pharmacy for a particular product. However, due to the nature of their business, the pharmacy could purchase that product from several sources and there is no reliable means of ensuring that the product being dispensed by the pharmacy when utilizing the wholesaler coupon was actually purchased by the pharmacy from the wholesaler being billed for the coupon benefit. The wholesaler doesn't want to fund a prescription coupon for product that it did not sell. There needs to be a reliable means, when determining eligibility of a prescription benefits request, to know if the product being utilized by the pharmacy was actually purchased by the pharmacy from the wholesaler being billed for the coupon benefit. If that did exist, there are wholesalers that would offer prescription coupons for some products.

Cash discount programs generally fit the description of an entity that has obtained a group of consumers for a lower cash price. The program has also negotiated a discount rate from one or more pharmacies in exchange for allowing the pharmacy to fill the prescriptions for the group of consumers. However, in some cases there are additional benefits available to the consumer, such as a pharmaceutical manufacturer coupon or rebate that the consumer of which the consumer is not aware.

Insurers that offer a prescription drug benefit to their members utilize a Prescription Benefits Manager (PBM) to administrate the prescription drug benefit, negotiate a better rate from pharmacies that provide prescription services and obtain access to pharmaceutical manufacturer rebates (rebates) for some brand name medications that are utilized by the insurer's members. The PBM utilizes many ways to obtain revenue from the insurer for their services including: retention of some or all of the discount negotiated from the pharmaceutical manufacturer, paying pharmacies less than what is billed to the insurer (a practice called "spread pricing" or "spread"), and administration fees charged to the insurer for the PBMs services. Larger insurers require the PBM to provide all of the rebates to the insurer, but there is no reliable means of validating that actually occurs. When the PBM does pass a rebate to the insurer, the funds arrive about 6 months after the prescription was filled and the insurer has no means of knowing for what drug, member or prescription the rebate relates to. Recently, PBMs have changed the definition of some of their revenue from rebates to other fees, such as "access fees" or "price protection fees" that are negotiated with pharmaceutical manufacturers. This change in definition protects that revenue from language with insurers that require the sharing or pass through of "rebates."

The practice of "spread pricing" was recently exposed in Ohio where the state auditor found that PBMs had retained more than $250 million during the year 2016 from the Ohio Medicaid program alone. This practice has been going on for many years but has just recently been noticed by a few large benefit providers. This attention has led the United States congress and some state legislatures to introduce laws that make the practice illegal. However, there exists no means of validating if it actually occurs or not, other than a retrospective audit of claims data.

Due to the lack of knowledge of availability and the lack of transparency, individual consumers in the United States do not have ready access to the knowledge of what a prescription will cost them after all available benefits have been applied at the various pharmacies that they could choose to fill the prescription. This lack of pricing knowledge has led consumers to abandon needed prescription medications because of the perception that they cannot afford it, when, in fact, if all benefits were applied properly, they could afford the medications. There is a need for an entity that could properly predict and present to a consumer the final amount due from the consumer at a selectable set of pharmacies after all benefits have been applied to the prescription prior to the consumer choosing the pharmacy to fill the prescription.

Due to this and other factors, a need exists in the marketplace for an entity that has knowledge of all of the benefits available to a particular consumer for a particular prescription and can create an individual transaction for each available benefit in the appropriate order while applying the previous benefit to the subsequent claim request. This entity will establish relationships with pharmacies, pharmaceutical manufacturers, wholesalers, insurers, and discount programs that will provide the information about the benefits that are available and allow for the creation and synchronization of the individual claims necessary to provide aggregated benefits to consumers in a real-time, automated fashion.

SUMMARY

Embodiments of the present invention address and overcome one or more of the above shortcomings and drawbacks, by providing methods, systems, and apparatuses related to identifying and providing aggregated prescription benefits to consumers of prescription products at the point of sale.

According to some embodiments, a computer-implemented method for managing prescription benefits in prescription claim or inquiry requests performed by one or more computers in a prescription order processing system includes receiving a prescription claim request related to a consumer from a requesting entity. A crosswalk file is retrieved that comprises information from a plurality of health plan member files describing benefits available to the consumer provided by a plurality of benefit providers. The crosswalk file is used to automatically determine an order submission sequence indicating an order in which claim or inquiry requests corresponding to the benefits are submitted to the benefit providers. The claim or inquiry requests are submitted to the benefit providers according to the order submission sequence. Responses from the benefit providers are automatically aggregated in order to generate an aggregated response to the prescription claim request. The aggregated response is transmitted to the requesting entity.

In some embodiments of the aforementioned method, the computers include a benefits aggregator computer that performs one or more of the automatic determination of the order submission sequence, the submission of the claim or inquiry requests, and the automatic aggregation of responses from the benefit providers. In other embodiments, the computers include a network switch computer that perform one or more of the automatic determination of the order submission sequence, the submission of the claim or inquiry requests, and the automatic aggregation of responses from the benefit providers.

In some embodiments of the aforementioned method, the prescription claim request comprises an identification of the consumer, a product for which a prescription order is being made, and prescriber who created the prescription order for the consumer. Additionally, the prescription claim request may include an indication of a dispensing entity which will provide the prescription order to the consumer.

In some embodiments, the order submission sequence is selected by evaluating a plurality of possible order submission sequences according to one or more selection criteria. This selection criterion may be, for example, reducing costs to the consumer related to fulfillment of the order. In one embodiment, the order submission sequence is selected using a graph search of possible order submission sequences performed using a graph where each benefit is represented as a node. In another embodiment, the order submission sequence is selected using a tree search of possible order submission sequences performed using a graph where each benefit is represented as a node. In some embodiments, the order submission sequence is generated prior to receiving the prescription claim request and the order submission response is stored in the crosswalk file.

According to another aspect of the present invention, an article of manufacture for managing prescription benefits in prescription claim or inquiry requests in a prescription order processing system comprises a non-transitory, tangible computer-readable medium holding computer-executable instructions for performing the methods discussed above.

According to another embodiment, a system for managing prescription benefits in prescription claim or inquiry requests in a prescription order processing system includes a database and one or more computers. The database stores a crosswalk file that comprises information from a plurality of health plan member files describing benefits available to the consumer provided by a plurality of benefit providers. The computers receive a prescription claim request related to a consumer from a requesting entity, and submit the claim or inquiry requests to the benefit providers according to an order submission sequence determined using the crosswalk file. The computers may further automatically aggregate responses from the benefit providers in order to generate an aggregated response to the prescription claim request, and transmit the aggregated response to the requesting entity.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there are shown in the drawings embodiments that are presently preferred, it being understood, however, that the invention is not limited to the specific instrumentalities disclosed. Included in the drawings are the following Figures:

FIG. 2 shows an example Health Plan (HP) or Prescription Discount Administrator (PDA) member file that may be used in some embodiments;

FIG. 3 shows example Member ID files that may be used in some embodiments;

FIG. 4B provides a textual description of the steps performed in FIG. 4A;

FIG. 4C provides additional textual description of the steps performed in FIG. 4A;

FIG. 5B provides a textual description of the steps performed in FIG. 5A;

FIG. 5C provides additional textual description of the steps performed in FIG. 5A;

FIGS. 6A-6C show another example embodiment in which a prescription consumer without insurance coverage presents a prescription order to the pharmacy or dispensing prescriber to be fulfilled;

DETAILED DESCRIPTION

Figure 1:
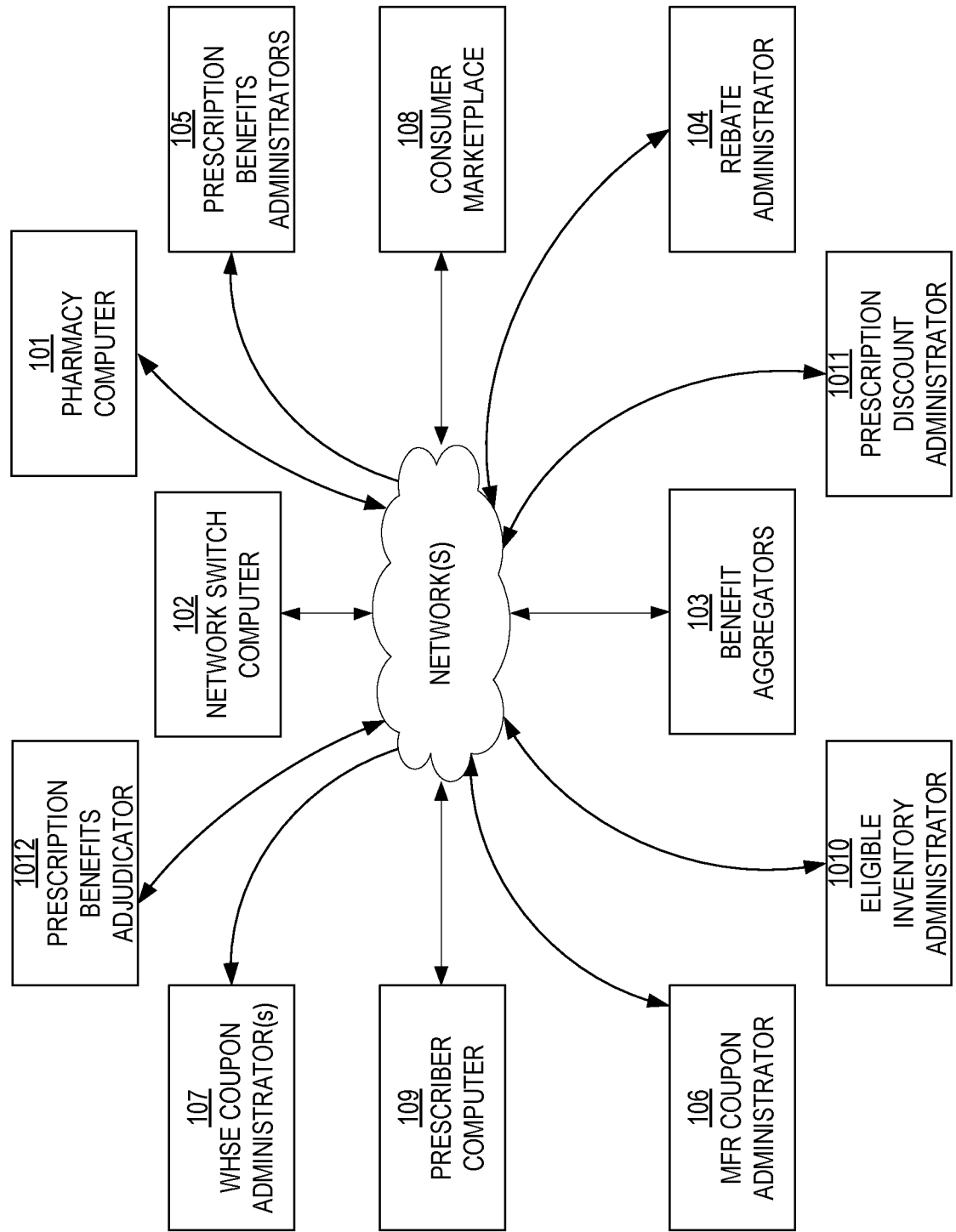
FIG. 1 shows an example system for prescription order processing, according to some embodiments.

Systems, methods, and apparatuses are described herein which relate generally to identifying and providing aggregated prescription benefits to consumers of prescription products at the point of sale.

Briefly, a computer system (described herein as the benefits aggregator) is used to identify the various benefits available to a consumer for an individual or group of products, sequence or cause to be sequenced the order in which claim or inquiry requests are submitted to the various benefit providers or benefit administrators, and aggregate the claim or inquiry responses from all related benefit providers or benefits administrators in order to provide an aggregated response to the originator of the claim or inquiry request or the prescription consumer. A healthcare benefit claim or inquiry request containing data elements that provide for the identification of the individual for whom the claim or inquiry request is being made, the product for which the claim or inquiry request is being made, the prescriber who created the prescription order containing the consumer, instruction, and product details, and (optionally) the dispensing entity which will provide the prescription order to the consumer, and (optionally) one of the benefit providers that may provide prescription benefits to the consumer to assist with the cost of the prescription order produced. Once the product, the consumer, the prescriber, and the dispensing entity is identified, the benefits aggregator identifies the prescription benefit provider(s) to whom the claim or inquiry request will need to be submitted as well as the priority in which the claim or inquiry request should be submitted to each prescription benefit provider in order to maximize savings and reduce costs throughout the process. After the prescription benefit providers and the sequencing priority has been identified, the benefits aggregator, or an entity enabled by or acting on behalf of the benefits aggregator, begins creating and sending claim or inquiry requests as well as receiving, recording, and interpreting claim or inquiry responses from the requests that were sent. The benefits aggregator may or may not utilize information in a preceding claim or inquiry response to populate a subsequent claim or inquiry request. After the final response has been received by the benefits aggregator or an entity enabled by or acting on behalf of the benefits aggregator, a response is created that may include the aggregated information from all related claim or inquiry requests and responses which is then forwarded back to the submitter of the original claim or inquiry request. The benefits aggregator then creates and submits a detailed claim or inquiry document that contains the results of each claim or inquiry response that was related to the previously generated aggregated response to the submitter of the original claim or inquiry request.

The following describes, in detail, the embodiments represented in the embodiment drawings of the invention with reference to the figures that are included. It should be understood by one skilled in the art that other embodiments may exist in different forms and this detailed description should not be limited to the embodiments described herein. The embodiments provided are for demonstration purposes only and are not intended to fully describe all cases in which it is possible for this invention to operate.

Figure 14:
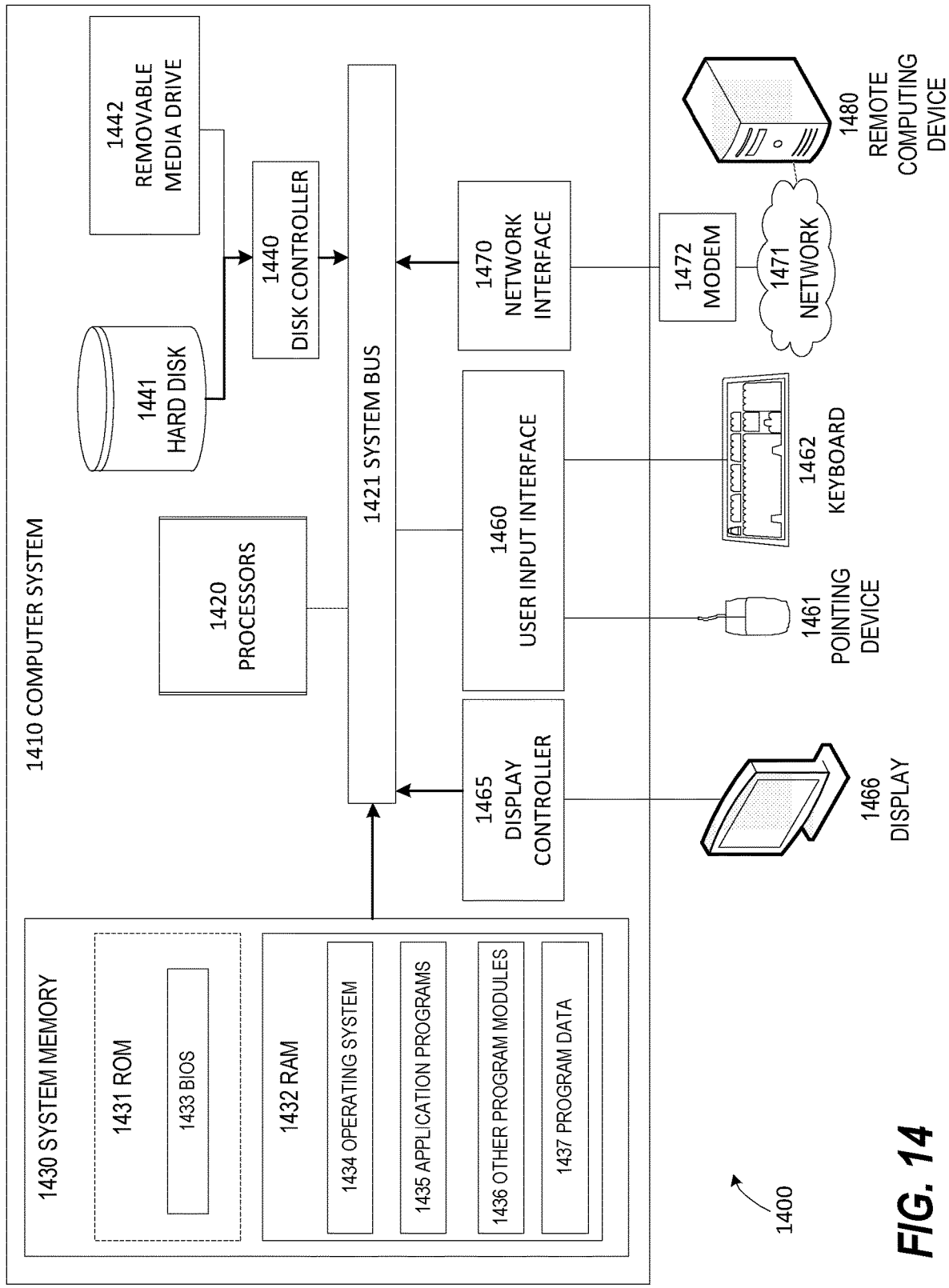
FIG. 14 illustrates an exemplary computing environment within which embodiments of the invention may be implemented.

FIG. 1 shows an example system for prescription order processing, according to some embodiments. Each of the entities shown in FIG. 1 comprises one or more computers. One example of a suitable computer system is shown in FIG. 14. The computers are each connected either directly or indirectly by one or more networks such as the Internet. The paragraphs that follow describe the function of each of these computers and how they interact for prescription order processing. These paragraphs refer to a "prescription consumer" that is a prescription consumer or a prescriber or other entity acting on behalf of the prescription consumer. More particularly, the prescription consumer is an entity that has in the past purchased, or intends to in the future to purchase, a prescription product from a pharmacy or dispensing prescriber.

Pharmacy Computer 101 also referred to herein as the Healthcare Provider (HCP), is located at the pharmacy, prescriber, or other submitter of prescription claims, according to some embodiments. The Pharmacy Computer 101 shown in FIG. 1 may be connected to the Network Switch Computer 102 which, in turn, connects the system to one or more of the following: Rebate Administrators 104, Prescription Benefits Administrator 105, Manufacturer Coupon Administrators 106, Wholesaler Coupon Administrators 107, other network switches, Benefits Aggregators 103, as well as consumer marketplaces, prescribers, and eligible inventory administrators, and prescription discount administrators (not shown in FIG. 1). It should be understood that there could be a plurality of network switch computers each either directly or indirectly linked together to provide access to all prescription benefits administrators (PBAs) that are not connected to the pharmacy, prescriber, or other submitter of prescription claims directly or to the internet provider of same. The system may be utilized to store patient, prescriber, product, and payer records as they pertain to an individual prescription consumer's prescription records, whether active or inactive and to submit and receive prescription benefit claims on the behalf of the prescription consumer. The system may also be utilized to exchange information from a prescriber, lab, hospital or other medical provider as it pertains to the prescription consumer. The information exchanged may include but is not limited to: electronic prescriptions, electronic prior authorization information, laboratory values, diagnosis codes and insurance membership, benefits, and claim details.

The Network Switch Computer 102 may provide various functions related to prescription distribution and management. For example, in some embodiments, the Network Switch Computer 102 is configured to allow for the smooth transmission of data between PBAs 105, other network switches, Benefits Aggregators 103, Consumer Marketplaces 108, and Prescriber Computers 109. The Network Switch Computer 102 may also verify, amend and re-direct prescription claim requests from entities such as pharmacies, Dispensing Prescribers, Benefits Aggregators 103, Consumer Marketplaces 108, and other network switch computers. Similarly, the Network Switch Computer 102 may verify, amend, and re-direct prescription claim responses from entities such as PBAs 105, Benefits Aggregators 103, Consumer Marketplaces 108, and other network switches computers.

The Benefits Aggregator 103 is configured to receive membership targeting information from a health plan, employer, manufacturer or wholesaler coupon sponsor, prescription discount program, or other provider or administrator of prescription benefits for use in identifying prescription claims that are directly related to the purchase request made through a pharmacy or dispensing prescriber by a member of a specific group of beneficiaries. The Benefits Aggregator 103 may provide claims targeting information to one or more network switches, pharmacy practice management systems, prescription benefits adjudicators, or other intermediary of prescription claim requests and responses. The Benefits Aggregator 103 further provides benefit plan design details to various administration computers as it relates to benefits that a provider of prescription benefits wishes to offer through the services of the benefits aggregator.

The Benefits Aggregator 103 provides prioritization, sequencing, creation, formatting and submission of prescription claim requests for primary or subsequent payers whether utilizing prior payer response information or some other source to populate the created prescription claim request. Additionally, the Benefits Aggregator 103 may provide program management and administrative services for prescription benefit providers. In some embodiments, the Benefits Aggregator 103 also provides the capability of processing benefit inquiry requests from one or more consumer marketplaces wherein a prescription consumer (individual or group) may request the aggregate benefit level and final cost associated with providing a product or group of products to a prescription consumer (individual or group).

The Rebate Administrator 104 receives, stores, and processes claim requests that are formatted in a standardized format, commonly the current National Council for Prescription Drug Plans (NCPDP) telecommunications standard, according to plan design rules that have been set by a program sponsor. The Rebate Administrator 104 also generates, stores, and communicates claim responses to claim requests with approval or denial of claim benefits along with the appropriate information supporting the approval or denial of benefits for further use by the submitter in communications, accounting, correcting, or further submission to additional benefit providers. This specific instance may be set up with program design rules set out by the product manufacturer, distributor, or some other entity within the supply chain that wishes to offer product rebates to a purchaser of the product or products, whether individual or group, for which the benefit may be provided in an electronic fashion The Prescription Benefits Administrator 105 receives, stores, and processes claim requests that are formatted in a standardized format, commonly the current NCPDP telecommunications standard, according to plan design rules that have been set by a program sponsor. The Prescription Benefits Administrator 105 also generates, stores, and communicates claim responses to claim requests with approval or denial of claim benefits along with the appropriate information supporting the approval or denial of benefits for further use by the submitter in communications, accounting, correcting, or further submission to additional benefit providers. This specific instance may be set up with program design rules set out by the insurance benefit provider from whom the final consumer may be eligible for prescription benefits.

The Manufacturer Coupon Administrator 106 receives, stores, and processes claim requests that are formatted in a standardized format, commonly the current NCPDP telecommunications standard, according to plan design rules that have been set by a program sponsor. The Manufacturer Coupon Administrator 106 also generates, stores, and communicates claim responses to claim requests with approval or denial of claim benefits along with the appropriate information supporting the approval or denial of benefits for further use by the submitter in communications, accounting, correcting, or further submission to additional benefit providers. This specific instance may be set up with program design rules set out by the product manufacturer that wishes to offer consumer benefit to a purchaser of the product or products for which the benefit may be provided in an electronic fashion The Wholesale (WHSE) Coupon Administrator 107 receives, stores, and processes claim requests that are formatted in a standardized format, commonly the current NCPDP telecommunications standard, according to plan design rules that have been set by a program sponsor. Additionally, the WHSE Coupon Administrator 107 generates, stores, and communicates claim responses to claim requests with approval or denial of claim benefits along with the appropriate information supporting the approval or denial of benefits for further use by the submitter in communications, accounting, correcting, or further submission to additional benefit providers. This specific instance may be set up with program design rules set out by the product distributor, wholesaler, or some other entity within the supply chain that wishes to offer consumer benefit to a purchaser of the product or products for which the benefit may be provided in an electronic fashion The Consumer Marketplace 108 provides prescription consumers or a related party the ability to create a personalized login that may contain, for example, permission for this computer to gain and maintain access to the prescription consumer's complete medical record, including prescription history, whether dispensed to the prescription consumer, being considered for order by a prescriber, or waiting to be dispensed to the prescription consumer or a related party. The personalized login may also include relational information between the prescription consumer and one or more parties that provide permission to the prescription consumer and for which the prescription consumer requests permission to have access to both parties' medical record. Additionally, in some embodiments, the personal login may contain one or more of: financial payment information, permission to use financial payment information for the purpose of funding any purchases that the prescription consumer or a related party may elect to make through this computer's capability or use, one or more prescription benefit information sets that may be used for identification of, submitting pricing inquiries for and claim submissions on behalf of the prescription consumer or a related party. Product options and the associated benefits available for a single or a plurality of products that are related to the treatment of a certain diagnosis, disease process, condition, syndrome, or other health related or genetically induced health condition. In some embodiments, the consumer marketplace computer 108 provides prescription consumers or a related person the ability to identify their prescription product quantity, prescriber, pharmacy or dispensing prescriber selection criteria, method of payment, and delivery method. The preceding list is for demonstration purposes only and is not meant to be all inclusive of every action the prescription consumer or related person may take.

In some embodiments, the Consumer Marketplace 108 allows a prescription consumer or a related party to submit prescription refill requests or other product purchase requests, whether or not related to a prescription or health care in general, to this computer which will then be processed throughout the entire network of computers to completion of delivery of product to the prescription consumer and providing payment of all costs involved with the purchase through all available benefit or payment means.

In other embodiments, the Consumer Marketplace 108 allows a prescriber to submit an inquiry that may be related but is not limited in relation to: the availability of prescription benefit coverage, availability of dispensing locations, availability of product inventory at the available dispensing locations, costs associated with any of the product options at the individual or group of dispensing locations (e.g., health plan costs, consumer costs, coupon or voucher availability, etc.).

In other embodiments, the Consumer Marketplace 108 allows a prescriber to submit a prescription order request and receive a response, either approval or denial, whether it be for a new product order or refill request through this computer and its associated communications connections to the dispensing location, whether a pharmacy, dispensing prescriber or other retail or wholesale outlet that is connected to this computer whether or not the product requires a prescription order. Additionally, in other embodiments, the consumer marketplace computer 108 may allow other electronic consumer marketplaces to provide interactive connectivity to this computer such that such entity can offer or provide products or services through a separate computerized marketplace.

FIG. 1 also shows an example Prescriber Computer 109. Briefly, the typical, but not exclusive use of the Prescriber Computer 109 is for a prescriber to provide electronic prescription orders to a dispensing facility or device. The dispensing facility or device could be but is not limited to a pharmacy, dispensing prescriber location, remote dispensing device or robotically controlled machine.

The Eligible Inventory Administrator 1010 stores and maintains a list of products and their associated available inventory quantities that may be available to the dispensing entity for which there may be a benefit available. The Eligible Inventory Administrator 1010 receives and stores inventory purchase records from manufacturers, wholesalers, distributors or any other reseller of product that wishes to offer consumer benefits for the product that are sold by that or a different entity. In some embodiments, the Eligible Inventory Administrator 1010 also receives and stores utilization records from the benefits administrator associated with the dispensing, use, or further distribution of product that is related to a consumer benefit that may have been provided to a consumer of the product.

Aside from the aforementioned features, in some embodiments, the Eligible Inventory Administrator, 1010, calculates and maintains remaining inventory records for which a consumer benefit may be available at the location or group of related locations that may purchase, provide, dispense, use, or distribute product. Additionally, the Eligible Inventory Administrator, 1010, may be configured to receive request inquiries as to the availability of remaining product in sufficient quantities to allow for the dispensing, distribution, or use of the product to which a consumer benefit may be available. In response to these inquiries, the Eligible Inventory Administrator, 1010, may send information as to the availability of remaining product in sufficient quantities to allow for the dispensing, distribution, or use of the product to which a consumer benefit may be available.

The Prescription Discount Administrator 1011 receives, stores, and processes claim requests that are formatted in a standardized format (e.g., the current NCPDP telecommunications standard) according to plan design rules that have been set by a program sponsor. In some embodiments, the Prescription Discount Administrator 1011 also generates, stores, and communicates claim responses to claim requests with approval or denial of claim benefits along with the appropriate information supporting the approval or denial of benefits for further use by the submitter in communications, accounting, correcting, or further submission to additional benefit providers. This specific instance may be set up with program design rules set out by an entity that may have access to prescription discounts from usual and customary pricing, whether related to funded or unfunded member participation in a program to which the consumer may previously have been enrolled, currently be enrolled, or in the future may become enrolled from whom the consumer may be eligible to receive a discounted price for prescription benefits.

The Prescription Benefits Adjudicator 1012 receives, stores, and processes claim requests that are formatted in a standardized format (e.g., the current NCPDP telecommunications standard, according to plan design rules that have been set by a program sponsor. Additionally, in some embodiments, the Prescription Benefits Adjudicator 1012 generates, stores, and communicates claim responses to claim requests with approval or denial of claim benefits along with the appropriate information supporting the approval or denial of benefits for further use by the submitter in communications, accounting, correcting, or further submission to additional benefit providers. This specific instance may be set up with program design rules set out by one or more of: the prescription discount benefit provider, the rebate benefit provider, the manufacture coupon benefit provider, the benefit aggregator) and the WHSE coupon benefit provider from whom the final consumer may be eligible for prescription benefits FIG. 2 shows an example Health Plan (HP) member file that contains information that may be provided by one or more prescription benefit providers. For example, prescription benefit providers may share files, databases, etc., containing this information with the Benefit Aggregator 103 and/or other components showed in FIG. 1. Alternatively, other entities (e.g., pharmacies, businesses, individuals, etc.) may share this information. The HP member file includes identifiers from the consumer marketplace or other entity with unique consumer identifiers, such as the NCPDP database, allowing for the identification of their members for participation in the aggregated prescription benefits program described herein and the appropriate benefit providers that are available to the consumer. For example, as shown in FIG. 2, the HP member file includes a bank identification number (BIN), Processor Control Number (PCN), and Group combination. The BIN, PCN, Group and Member ID are used to determine the address to which the claim should be sent, the member database within the target computer receiving the claim that houses the eligibility file and, along with other items in the claim such as date of birth, gender, and more, match the person requesting claim eligibility the eligibility file for the benefit providers. The BIN is a six-digit number that health plans can use to process electronic pharmacy claims. The PCN is a second identifier that is used for routing claims. Finally the Group identifies the group from among other groups insured by the same company.

FIG. 3 shows example generated ("GEN") member files illustrating how the information contained in the HP member file may be utilized by the aggregated prescription benefits program described herein in order to create a complete consumer identification record across all transactions, product or service providers, and benefit providers associated with the aggregated prescription benefits program functionality. A GEN member file may be generated as follows. First the HP member file is parsed to extract all of the elements contained therein. The method of parsing and extraction depends on how the data is stored. For example, for a database structure, an identifier (e.g., the HP Member ID) is used to index into the database and retrieve all related information. For spreadsheet implementations, data can be extracted from the rows and columns using techniques generally known in the art. An algorithm is used to generate an alpha-numeric member ID referred to herein as the GEN member ID. This algorithm may be proprietary (as in the example of FIG. 3) or techniques known in the art may be utilized (e.g., combining a hash output with a timestamp) to generate the unique ID. The GEN member file is, in very basic terms, similar to the Index number for a row of data within a database table. This GEN member number will be related to each of the involved benefit administrator's Member ID information sets, the personal, geographic and demographic information for each person contained in the database table or tables. This GEN member number will be the common identifier within the benefit providers' eligibility tables (HP), Consumer Marketplace member files, or other member identifying database(s) that allows the linking of the persons within each of them. The GEN member number will be created by utilizing statistical methods that identify the same person across multiple database tables, matching them and assigning a single GEN member number to each individual. In this fashion, the master GEN member file will contain the GEN member number, the index number for the line of data, and the identity of the database table for each of the index numbers creating a crosswalk that will enable a single GEN member number to identify the same person in multiple member databases involving multiple benefit providers, consumer marketplaces, pharmacies, or prescribers. Once generated, the GEN member ID is assigned to the appropriate BIN, PCN, and Group combination (as determined by the HP member file). The HP member file is then linked to a crosswalk file (the "UPI crosswalk file" in FIG. 3). As is generally understood in the art, the term crosswalk refers to a mapping between equivalent elements (fields) in multiple database schemas. The crosswalk file thus provides a mapping between the HP member plan file and the information in the UPI file. Multiple HP member plan files (e.g., one for each benefit provider) may be linked in this form. The Member ID files may also store identifiers that make it possible, in the aggregated form, to identify the consumers in the consumer marketplace for determination of available benefits.

In some embodiments the UPI Crosswalk File will have automatically generated data elements that indicate the sequence in which the plurality of claims should be submitted. One example is as follows: A HP submits a HP member file to the Benefits Aggregator containing the identification elements for all of its eligible members. The GEN member ID assigned to each member and subsequently populated into the UPI Crosswalk File will contain an element that indicates that the claims for each of these identified members should be first sent to the Manufacturer Rebate Administrator for benefit determination. If benefits are provided, the benefit amount payable by the Manufacturer Rebate Administrator should then be applied to the total value of the claim resulting in a remaining value that is the remainder after subtracting the Manufacturer Rebate benefit from the total claim value. Subsequently, the claim should be sent to the Prescription Benefits Administrator, the Manufacturer Coupon Administrator and the WHSE Coupon Administrator respectively and those benefits applied in similar, waterfall, fashion. Information in the UPI Crosswalk File will also indicate if the claim should be re-sequenced to the Manufacturer Rebate Administrator, the Prescription Discount Administrator, the Manufacturer Coupon Administrator, and the WHSE Coupon Administrator should the claim to the Prescription Benefits Administrator fail to result in an approved response. This second pathway would provide the prescription consumer with the greatest out of pocket cost reduction possible if, for some reason, the prescription insurance benefit is not available for that particular prescription at that particular time.

The NCPDP Telecommunications Standard Payer Sheet Format Template includes all data fields that are available for use in a Payer Sheet that is created by a Benefits Administrator. This is an electronic claim form and the template describes the fields that can be used to create the customized form. The complete document is available at http//ncpdp.org/Resources/Hipaa.aspx. (under the section Telecommunication Version D.0).

Figure 4A:
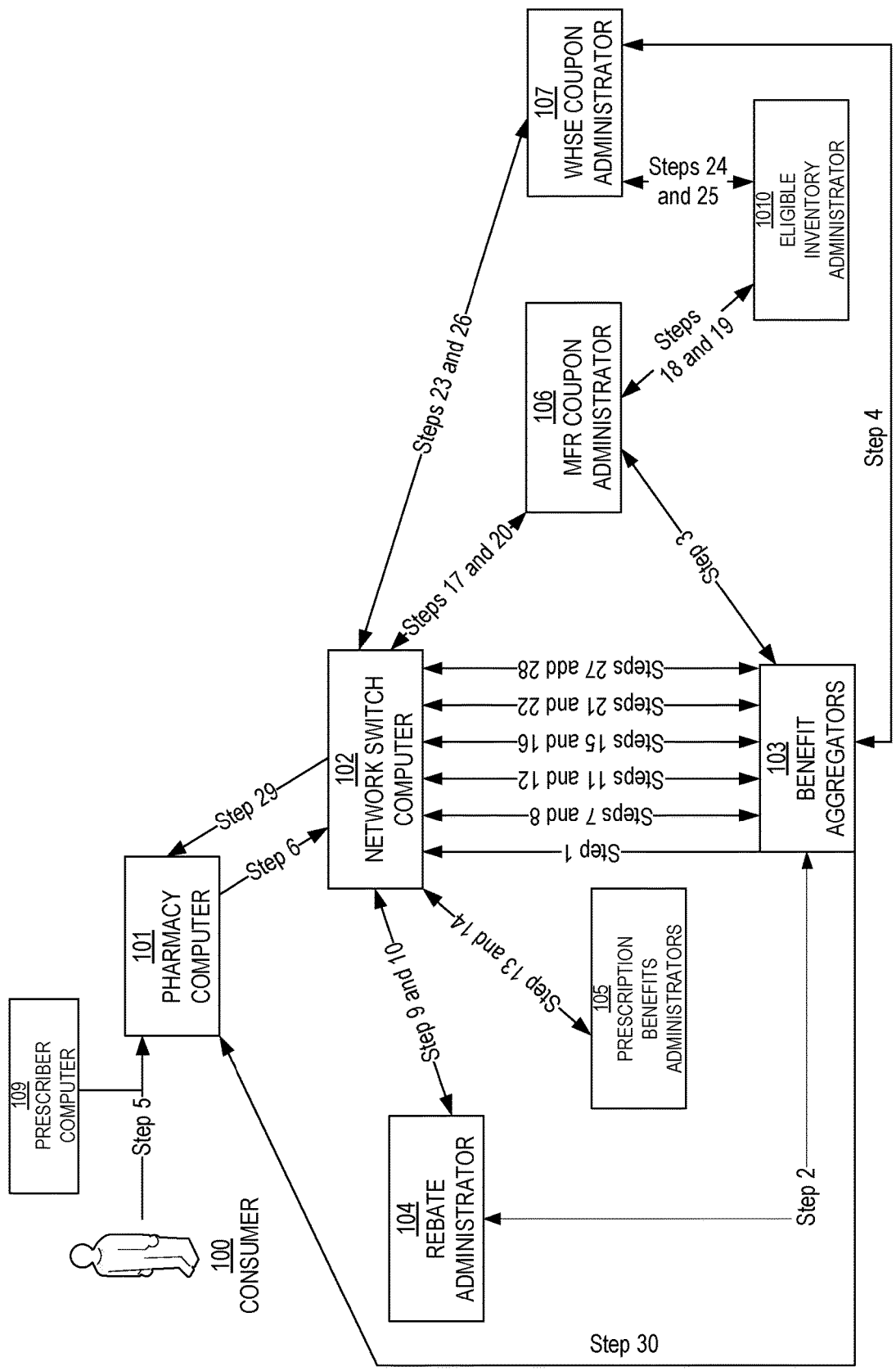
FIG. 4A illustrates an example of an embodiment in which a prescription consumer with insurance coverage presents a prescription order to the pharmacy or dispensing prescriber to be fulfilled.

FIG. 4 illustrates an example embodiment in which a prescription consumer with insurance coverage, either him/herself or an entity acting on the prescription consumer's behalf such as an electronic prescription communication service presents a prescription order to the pharmacy or dispensing prescriber to be fulfilled. Each step represents an action performed at that location and the submission of the claim to the next entity in the continuum to the end of the description. If any of the steps fail to result in an approved response or completed action, the other steps in the continuum may either continue or the process may proceed in reverse order to the originator with a message being provided to the HCP to make corrections to the submission request or for provision to the prescription consumer as to why the prescription benefit claim request was not successful; one example is as follows: (a) steps 1 through 9 are successful; (b) step 10 fails due to the prescription consumer's insurance benefit being expired; and (c) steps 7 through 9 are reversed. The Pharmacy Computer 101 is provided with a message advising the prescription consumer of the unavailability of prescription benefits due to expired coverage.

In the example of FIG. 4, the Benefits Aggregator 103 may be engaged by one or more benefits administrator computers 104, 105, 106, 107, 1011 to provide aggregation, sequencing, and/or administration services for prescription consumers that may be beneficiaries of the benefits provided by that entity. The prescription benefit providers may supply to the benefits aggregator a means of identifying prescription consumers that may be eligible to receive benefits. In addition, the prescription benefit provider may provide to the benefits aggregator the rulesets that determine if the prescription claim or inquiry request, the associated product and prescription consumer is eligible to receive benefits and what level of benefits are to be provided if eligible.

The Benefits Aggregator 103 supplies various information to the Network Switch Computer 102 (and other network switches, if used) to facilitate the identification of potentially eligible inquiries or claims requests for entry into the aggregated prescription benefits program. The Benefits Aggregator 103 or other entity performing program administration services for the benefits administrator computers 104, 105, 106, 107, 1011 sets up program design details in one or more administration computers in order to complete the successful administration of prescription claim or inquiry requests.

The Pharmacy Computer 101 receives a prescription order from or on the behalf of a Prescription Consumer 100 whether from manual data entry by a human or machine or transmitted in electronic form over some communication interface such as an electronic prescription network. The Pharmacy Computer 101 formats the prescription order into an electronic benefit claim request defined by a prescription benefits administrator computers 105, 104, 106, 107, 1011 which may be in the form of a payer sheet and submits it to the Network Switch Computer 102 to have the data contained therein checked for accuracy and appropriateness and to utilize the Network Switch Computer 102 connection to one or more of the various benefits administrator, aggregator, or adjudicator computers (103, 104, 105, 106, 107, 1011, and 1011). The Network Switch Computer 102 interrogates the electronic benefit claim request for identifying characteristics that are provided to the Network Switch Computer 102 from the Benefits Aggregator 103 using a data file, internal database, or remote connection to an external database. If the electronic benefit claim request meets the requirements of identification, it is then targeted for further action and may be forwarded to the Benefits Aggregator, 103. The Benefits Aggregator Computer 103 comprises a listing of instructions relating to the benefits that may be available for the electronic benefit claim request and the order in which one or more requests must be made to one or more benefit administrator(s). In another iteration, this list of instructions and ordering information may be housed at the Network Switch Computer 102.

In the example of FIG. 4, it is understood that the claim must first be formatted as a primary claim request containing data that is obtained from the GEN Member ID file utilizing the UPI Crosswalk File or some other data source, the initial claim request, databases or information sources from outside the claim request data, and the payer sheet as defined by the Rebate Administrator 104 and re-priced, if necessary, in accordance with a previously agreed upon reimbursement rate between the pharmacy and the benefits aggregator or Rebate Administrator utilizing the most recently published Average Wholesale Price (AWP), Wholesale Acquisition Cost (WAC), or other commercially or publicly available standard pricing element as published in a commercially or publicly available drug pricing database and a formula for reimbursement pricing, and populated according to the payer sheet defined by the Rebate Administrator 104. The benefit claim request is then submitted back to the Network Switch Computer 102 to be forwarded to the Rebate Administrator 104 for benefits consideration ("Claim One").

Upon approval of the benefits claim request, the Rebate Administrator 104 populates an approved claim response including, among other items, the dollar amount that will be paid to the submitting pharmacy and the remaining amount that is the responsibility of the prescription consumer and returns the approved claim response to the Network Switch Computer 102 for return to the submitting Pharmacy Computer 101.

Upon denial of the benefits claim request, the Rebate Administrator 104 populates a rejected claim response that details, among other things, the reason the claim was rejected and failed to produce an approved benefit claim response and returns the claim to the Network Switch Computer 102 for return to the Pharmacy Computer 101.

Upon receiving a denied claim response from the Rebate Administrator 104, the Network Switch Computer 102 identifies the claim as originating at the Benefits Aggregator Computer 103 and redirects the response to the Benefits Aggregator computer 103. The Benefits Aggregator Computer 103 consults the UPI Crosswalk File for determination of continuing in the process to the next benefit claim administrator or reversing any prior process and returning the rejected response to the Network Switch Computer 102 to be forwarded to the Pharmacy Computer 101.

Upon receiving an approved claim response from the Rebate Administrator 104, the Network Switch Computer 102 identifies the response claim as originating from the Benefits Aggregator Computer 103 and redirects the response to the Benefits Aggregator Computer 103. The Benefits Aggregator Computer 103, matches the response to the original benefit claim request, stores the benefits claim response and may extract from it any information necessary to populate an additional benefit claim request, consults the UPI Crosswalk File to identify further claim requests that need to occur, such as the Prescription Benefits Administrator 105, obtains other information necessary to populate the additional benefits claim request that is not present in the rebate administrator's response from the GEN Member ID file database or some other data source, creates a new claim request according to the payer sheet specified by the Prescription Benefits Administrator 105 and forwards the claim request to the Network Switch Computer 102 to be forwarded to the Prescription Benefits Administrator 105 for eligibility and benefits determination ("Claim Two"). The Prescription Benefits Administrator 105 may approve or deny the claim for benefits.

Upon denial of the benefits claim request, the Prescription Benefits Administrator 105 populates a rejected claim response that details, among other things, the reason the claim was rejected and failed to produce an approved benefit claim response and returns the claim to the Network Switch Computer 102 for return to the Pharmacy Computer 101.

Upon receiving a denied claim response from the Prescription Benefits Administrator 105, the Network Switch Computer 102 identifies the claim as originating at the Benefits Aggregator Computer 103 and redirects the response to the Benefits Aggregator computer 103. The Benefits Aggregator Computer 103 consults the UPI Crosswalk File, for determination of continuing in the process to the next benefit claim administrator or reversing any prior process and returning the rejected response to the Network Switch Computer 102 to be forwarded to the Pharmacy Computer 101.

Upon approval of the benefits claim request, the Prescription Benefits Administrator 105 populates an approved claim response including, among other items, the dollar amount that will be paid to the submitting pharmacy and the remaining amount that is the responsibility of the prescription consumer and returns the approved claim response to the Network Switch Computer 102 for return to the submitting Pharmacy Computer 101.

Upon receiving an approved claim response from the Prescription Benefits Administrator 105, the Network Switch Computer 102 identifies the claim as originating at the Benefits Aggregator Computer 103 and redirects the response to the Benefits Aggregator computer 103. The Benefits Aggregator 103 identifies the response claim as originating from the original benefit claim request, stores the benefits claim response and may extract from it any information necessary to populate an additional benefit claim request, obtains other information necessary to populate the additional benefits claim request that is not present in the rebate administrator's response from the Member ID file or some other data source, creates a new claim request according to the payer sheet specified by the Manufacturer Coupon Administrator 106 and forwards the claim request to the Network Switch Computer 102 for submission to the Manufacturer Coupon Administrator 106 for eligibility and benefits determination ("Claim Three"). The Manufacturer Coupon Administrator 106 may approve or deny the claim for benefits.

Upon receipt of the benefits claim request from the Network Switch Computer 102, the Manufacturer Coupon Administrator 106, may identify within the claim request one or more data elements which may include: From the HEADER segment: SERVICE PROVIDER ID QUALIFIER (FIELD 202-B2), SERVICE PROVIDER ID (FIELD 201-B1), DATE OF SERVICE (FIELD 401-D1), From the Claim Segment: PRODUCT/SERVICE ID QUALIFIER (FIELD 436-E1), PRODUCT/SERVICE ID (FIELD 407-D7), QUANTITY DISPENSED (FIELD 442-E7), COMPOUND CODE (FIELD 406-D6). From the various segments and data elements on the claim request as well as the instruction set sent to the manufacturer coupon administrator computer by the Benefits Aggregator 103, and the Member ID file, the Manufacturer Coupon Administrator 106 creates a query for approval to provide benefits for the product requested, in the amount requested, by the Pharmacy Computer 101 requesting it, at the time requested and submits the request to the Eligible Inventory Administrator 1010 (see e.g., FIG. 1).

The Eligible Inventory Administrator 1010 (see e.g., FIG. 1) consults the database containing the data describing the available inventory remaining of that specific product, at the time requested, for the quantity requested at or associated with the SERVICE PROVIDER ID (FIELD 407-D7) or Pharmacy Computer 101 requesting it and provides an approved or denied response to the Manufacturer Coupon Administrator 106.

Upon receipt of a denied response to provide benefits based on remaining inventory from the Eligible Inventory Administrator 1010 (see e.g., FIG. 1) by the Manufacturer Coupon Administrator 106, the Manufacturer Coupon Administrator 106 denies the benefit claim request and sends a rejected claim response to the Network Switch Computer 102 for return to the Pharmacy Computer 101 according to the payer sheet defined by the Manufacturer Coupon Administrator 106.

Upon receipt of an approved response to provide benefits based on remaining inventory from the Eligible Inventory Administrator 1010 (see e.g., FIG. 1) by the Manufacturer Coupon Administrator 106, the Manufacturer Coupon Administrator 106 proceeds with the other rulesets that will determine the final approval or denial status of the claim request.

Upon denial of the benefits claim request, the Manufacturer Coupon Administrator 106 populates a rejected claim response that details, among other things, the reason the claim was rejected and failed to produce an approved benefit claim response and returns the claim to the Network Switch Computer 102 for return to the Pharmacy Computer 101.

Upon receiving a denied claim response from the Manufacturer Coupon Administrator 106, the Network Switch Computer 102 identifies the claim as originating at the Benefits Aggregator Computer 103 and redirects the response to the Benefits Aggregator computer 103. The Benefits Aggregator Computer 103 consults the UPI Crosswalk File, for determination of continuing in the process to the next benefit claim administrator or reversing any prior process and returning the rejected response to the Network Switch Computer 102 to be forwarded to the Pharmacy Computer 101.

Upon receiving an approved claim response from the Manufacturer Coupon Administrator 106, the Network Switch Computer 102 identifies the claim as originating at the Benefits Aggregator Computer 103 and redirects the response to the Benefits Aggregator computer 103. If no further available benefits are indicated in the Member ID file database or some other data source, Upon receipt of the benefits claim request from the Network Switch Computer 102, the Manufacturer Coupon Administrator 106, may identify within the claim request one or more data elements which may include: From the HEADER segment: SERVICE PROVIDER ID QUALIFIER (FIELD 202-B2), SERVICE PROVIDER ID (FIELD 201-B1), DATE OF SERVICE (FIELD 401-D1), From the Claim Segment: PRODUCT/SERVICE ID QUALIFIER (FIELD 436-E1), PRODUCT/SERVICE ID (FIELD 407-D7), QUANTITY DISPENSED (FIELD 442-E7), COMPOUND CODE (FIELD 406-D6). From the various segments and data elements on the claim request as well as the instruction set sent to the manufacturer coupon administrator computer by the Benefits Aggregator 103, and the Member ID file, the Manufacturer Coupon Administrator 106 creates a query for approval to provide benefits for the product requested, in the amount requested, by the Pharmacy Computer 101 requesting it, at the time requested and submits the request to the Eligible Inventory Administrator 1010 (see e.g., FIG. 1).

The Eligible Inventory Administrator 1010 (FIG. 1) consults the database containing the data describing the available inventory remaining of that specific product, at the time requested, for the quantity requested at or associated with the SERVICE PROVIDER ID (FIELD 407-D7) or Pharmacy Computer 101 requesting it and provides an approved or denied response to the Manufacturer Coupon Administrator 106.

Upon receipt of a denied response to provide benefits based on remaining inventory from the Eligible Inventory Administrator 1010 (see e.g., FIG. 1) by the Manufacturer Coupon Administrator 106, the Manufacturer Coupon Administrator 106 denies the benefit claim request and sends a rejected claim response to the Network Switch Computer 102 for return to the Pharmacy Computer 101 according to the payer sheet defined by the Manufacturer Coupon Administrator 106.

Upon receipt of an approved response to provide benefits based on remaining inventory from the Eligible Inventory Administrator 1010 (see e.g., FIG. 1) by the Manufacturer Coupon Administrator 106, the Manufacturer Coupon Administrator 106 proceeds with the other rulesets that will determine the final approval or denial status of the claim request.

Upon approval of the benefits claim response, the Manufacturer Coupon Administrator 106 populates a benefit claim response that details, among other things, the dollar amount that will be paid to the original submitting pharmacy and the amount to be collected from the prescription consumer and returns the claim to the Network Switch Computer 102 for return to the Pharmacy Computer 101.

Upon denial of the benefits claim request, the Manufacturer Coupon Administrator 106 populates a rejected claim response that details, among other things, the reason the claim was rejected and failed to produce an approved benefit claim response and returns the claim to the Network Switch Computer 102 for return to the Pharmacy Computer 101.

Upon receiving a denied claim response from the Manufacturer Coupon Administrator 106, the Network Switch Computer 102 identifies the claim as originating at the Benefits Aggregator Computer 103 and redirects the response to the Benefits Aggregator computer 103. The Benefits Aggregator Computer 103 consults the UPI Crosswalk File, for determination of continuing in the process to the next benefit claim administrator or reversing any prior process and returning the rejected response to the Network Switch Computer 102 to be forwarded to the Pharmacy Computer 101.

Upon receiving an approved claim response from the Manufacturer Coupon Administrator 106, the Network Switch Computer 102 identifies the response claim as originating from the Benefits Aggregator Computer 103, and redirects the response to the Benefits Aggregator computer 103. The Benefits Aggregator 103 identifies the response claim as originating from the original benefit claim request, stores the benefits claim response and may extract from it any information necessary to populate an additional benefit claim request, obtains other information necessary to populate the additional benefits claim request that is not present in the rebate administrator's response from the UPI Crosswalk File database or other data source, creates a new claim request according to the payer sheet specified by the WHSE Coupon Administrator 107 ("Claim Four") and forwards the claim request to the WHSE Coupon Administrator 107 for eligibility and benefits determination. The WHSE Coupon Administrator 107 may approve or deny the claim for benefits. If no further available benefits are indicated in the Member ID file database or some other data source, the (manufacturer coupon administrator 106 or WHSE Coupon Administrator 107) returns the claim to the Network Switch Computer 102 for return to the Pharmacy Computer 101).

Upon receipt of the benefits claim request from the Network Switch Computer 102, the WHSE Coupon Administrator 107, may identify within the claim request one or more data elements which may include: From the HEADER segment: SERVICE PROVIDER ID QUALIFIER (FIELD 202-B2), SERVICE PROVIDER ID (FIELD 201-B1), DATE OF SERVICE (FIELD 401-D1), From the Claim Segment: PRODUCT/SERVICE ID QUALIFIER (FIELD 436-E1), PRODUCT/SERVICE ID (FIELD 407-D7), QUANTITY DISPENSED (FIELD 442-E7), COMPOUND CODE (FIELD 406-D6). From the various segments and data elements on the claim request as well as the instruction set sent to the WHSE Coupon Administrator 107 by the Benefits Aggregator 103, and the Member ID file, the WHSE Coupon Administrator 107 creates a query for approval to provide benefits for the product requested, in the amount requested, by the Pharmacy Computer 101 requesting it, at the time requested and submits the request to the Eligible Inventory Administrator 1010 (see e.g., FIG. 1).

The Eligible Inventory Administrator 1010 (see e.g., FIG. 1) consults the database containing the data describing the available inventory remaining of that specific product, at the time requested, for the quantity requested at or associated with the SERVICE PROVIDER ID (FIELD 407-D7) or Pharmacy Computer 101 requesting it and provides an approved or denied response to the WHSE Coupon Administrator 107.

Upon receipt of a denied response to provide benefits based on remaining inventory from the Eligible Inventory Administrator 1010 (see e.g., FIG. 1) by the WHSE Coupon Administrator 107, the WHSE Coupon Administrator 107 denies the benefit claim request and sends a rejected claim response to the Network Switch Computer 102 for return to the Pharmacy Computer 101 according to the payer sheet defined by the WHSE Coupon Administrator 107.

Upon receipt of an approved response to provide benefits based on remaining inventory from the Eligible Inventory Administrator 1010 (see e.g., FIG. 1) by the WHSE Coupon Administrator 107, the WHSE Coupon Administrator 107 proceeds with the other rulesets that will determine the final approval or denial status of the claim request.

Upon approval of the benefits claim request, the WHSE Coupon Administrator 107 populates a benefit claim response that details, among other things, the dollar amount that will be paid to the original submitting pharmacy and the amount to be collected from the prescription consumer and returns the claim to the Network Switch Computer 102 for return to the Pharmacy Computer 101.

Upon denial of the benefits claim request, the WHSE Coupon Administrator 107 populates a rejected claim response that details, among other things, the reason the claim was rejected and failed to produce an approved benefit claim response and returns the claim to the Network Switch Computer 102 for return to the Pharmacy Computer 101.

Upon receiving a denied claim response from the WHSE Coupon Administrator 107, the Network Switch Computer 102 identifies the claim as originating at the Benefits Aggregator Computer 103 and redirects the response to the Benefits Aggregator computer 103. The Benefits Aggregator Computer 103 consults the UPI Crosswalk File, for determination of continuing in the process to the next benefit claim administrator or reversing any prior process and returning the rejected response to the Network Switch Computer 102 to be forwarded to the Pharmacy Computer 101.

Upon receiving an approved claim response from the WHSE Coupon Administrator 107, the Network Switch Computer 102 identifies the response claim as originating from the Benefits Aggregator Computer 103 and redirects the response to the Benefits Aggregator computer 103. The Benefits Aggregator 103 identifies the response claim as originating from the original benefit claim request, stores the benefits claim response and may extract from it any information necessary to populate an additional benefit claim request, obtains other information necessary to populate the additional benefits claim request that is not present in the rebate administrator's response from the UPI Crosswalk File database or other data source.

If no further available benefits are indicated in the UPI Crosswalk File database or some other data source, the Benefits Aggregator 103 aggregates the sum of the payable amounts indicated on each approved claim response from the various benefits administration computers, populates the sum amount and the final amount due from the prescription consumer into a response to the original claim request, and returns the approved claim response to the Network Switch Computer 102 for return to the Pharmacy Computer 101).

The Pharmacy Computer 101 collects the final amount owed by the prescription consumer and provides the fulfilled prescription order to the prescription consumer.

The Network Switch Computer 102 or the Benefits Aggregator 103 then creates a data file that identifies the aggregated claim from all others and also contains each individual benefit claim response from each of the Rebate Administrator 104 (herein "Claim One"), Prescription Benefits Administrator 105 (herein "Claim Two"), Manufacturer Coupon Administrator 106 (herein "Claim Three"), and the WHSE Coupon Administrator 107 (herein "Claim Four"). This data file will be utilized by the pharmacy or an entity acting on behalf of the pharmacy to reconcile payments as they arrive to the individual claims that occurred as a result of the original claim request. Either the Benefits Aggregator 103 or the individual benefits administrator computers (104, 105, 106, 107, 1011) will create and send documentation along with the payment for approved claims to the Pharmacy Computer 101 or the Prescription Consumer 100 for identification of the individual claims or inquiries that were processed as a part of the aggregated response and the level of benefit that was provided as part of the aggregated response.

Each of the claim responses may also be communicated to one or more of any of the benefits administrators as informational data concerning the claim in which that benefit administrator was involved in providing a financial benefit to the prescription consumer for at least a portion of the cost of the prescription.

It should be noted that each claim request that is created along with the transmission, processing, response, sequencing, subsequent claim creation, transmission, processing, response, continuing until no additional claims need be created in association with the original claim request, the final aggregated claim response creation and return to the pharmacy must occur within the time that the connection with the pharmacy for the original request is still open; usually less than fifteen seconds.

Figure 5A:
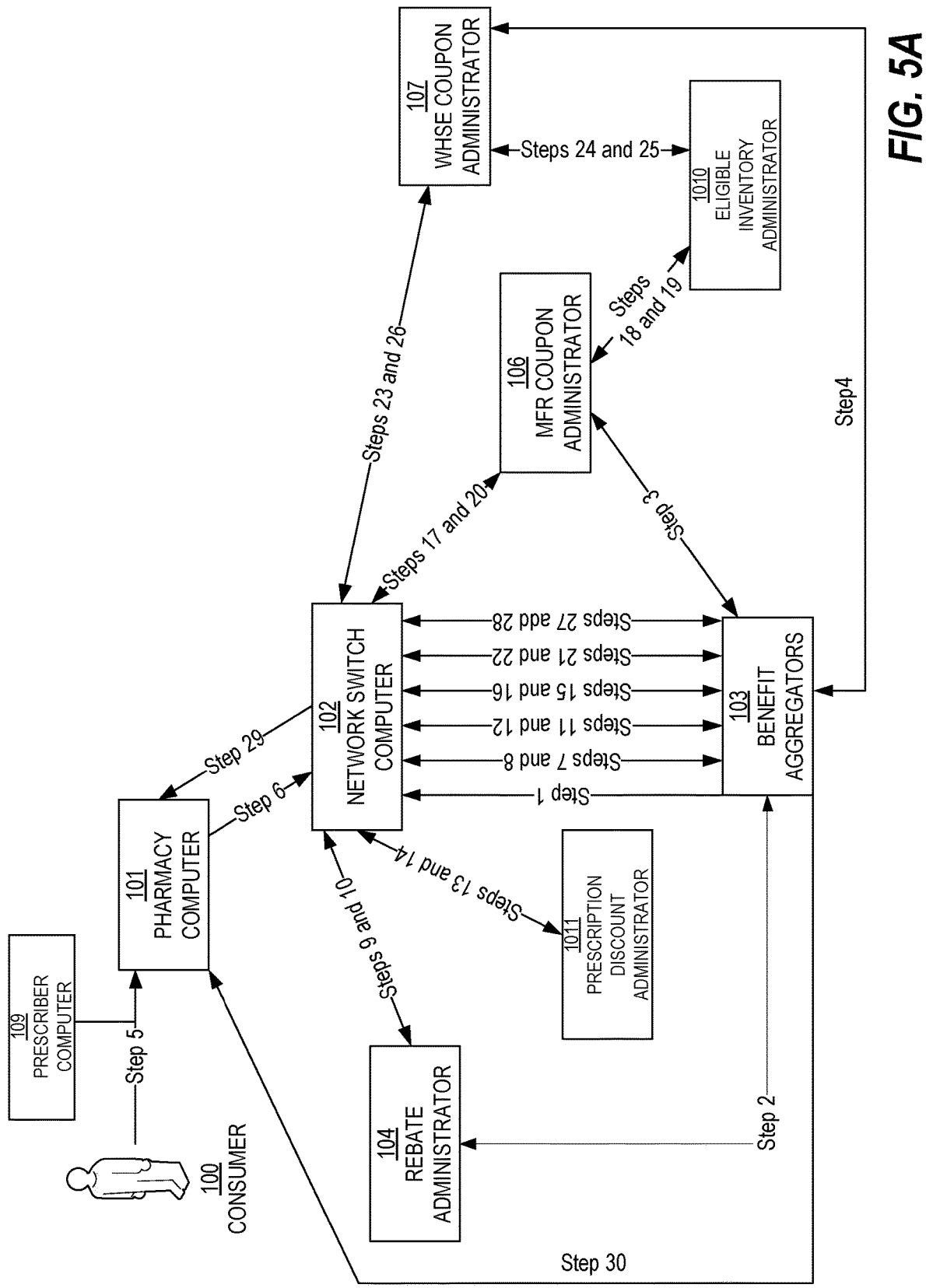
FIG. 5A shows an example embodiment in which a prescription consumer without insurance coverage presents a prescription order to the pharmacy or dispensing prescriber to be fulfilled.

FIG. 5 illustrates an example embodiment in which a prescription consumer without insurance coverage, either him/herself or an entity acting on the prescription consumer's behalf such as an electronic prescription communication service presents a prescription order to the pharmacy or dispensing prescriber to be fulfilled. Each step represents an action performed at that location and the submission of the claim to the next entity in the continuum to the end of the description. If any of the steps fail to result in an approved response or completed action, the other steps in the continuum may either continue or the process may proceed in reverse order to the originator with a message being provided to the HCP to make corrections to the submission request or for provision to the prescription consumer as to why the prescription benefit claim request was not successful; one example is as follows: (a) steps 1 through 9 are successful; (b) step 10 fails due to the prescription consumer's insurance benefit being expired; and (c) steps 7 through 9 are reversed. The Pharmacy Computer 101 is provided with a message advising the prescription consumer of the unavailability of prescription benefits due to expired coverage.

In the example of FIG. 5 the Benefits Aggregator 103 may be engaged by one or more benefits administrator computers 104, 106, 107, 1010, 1011 to provide aggregation, sequencing, and/or administration services for prescription consumers that may be beneficiaries of the benefits provided by that entity. The prescription benefit providers may supply to the benefits aggregator a means of identifying prescription consumers that may be eligible to receive benefits. In addition, the prescription benefit providers may provide to the benefits aggregator the rulesets that determine if the prescription claim or inquiry request, the associated product and prescription consumer is eligible to receive benefits and what level of benefits are to be provided if eligible.

The Benefits Aggregator 103 supplies various information to the Network Switch Computer 102 (and other network switches, if used) to facilitate the identification of potentially eligible inquiries or claims requests for entry into the aggregated prescription benefits program. The Benefits Aggregator 103 or other entity performing program administration services for the benefits administrator computers 104, 106, 107, 1010, 1011 sets up program design details in one or more administration computers in order to complete the successful administration of prescription claim or inquiry requests.

The Pharmacy Computer 101 receives a prescription order from or on the behalf of a Prescription Consumer 100 whether from manual data entry by a human or machine or transmitted in electronic form over some communication interface such as an electronic prescription network. The Pharmacy Computer 101 formats the prescription order into an electronic benefit claim request defined by a prescription benefits administrator computers 104, 106, 107, 1010, 1011 which may be in the form of a payer sheet and submits it to the Network Switch Computer 102 to have the data contained therein checked for accuracy and appropriateness and to utilize the Network Switch Computer 102 connection to one or more of the various benefits administrator, aggregator, or adjudicator computers (103, 104, 106, 107, 1010, and 1011). The Network Switch Computer 102 interrogates the electronic benefit claim request for identifying characteristics that are provided to the Network Switch Computer 102 from the Benefits Aggregator 103 using a data file, internal database, or remote connection to an external database. If the electronic benefit claim request meets the requirements of identification, it is then targeted for further action and may be forwarded to the Benefits Aggregator, 103. The Benefits Aggregator Computer 103 comprises a listing of instructions relating to the benefits that may be available for the electronic benefit claim request and the order in which one or more requests must be made to one or more benefit administrator(s). In another iteration, this list of instructions and ordering information may be housed at the Network Switch Computer 102.

In the example of FIG. 5, it is understood that the claim must first be formatted as a primary claim request containing data that is obtained from the GEN Member ID file utilizing the UPI Crosswalk File or some other data source, the initial claim request, databases or information sources from outside the claim request data, and the payer sheet as defined by the Rebate Administrator 104 and re-priced, if necessary, in accordance with a previously agreed upon reimbursement rate between the pharmacy and the benefits aggregator or Rebate Administrator utilizing the most recently published Average Wholesale Price (AWP), Wholesale Acquisition Cost (WAC), or other commercially or publicly available standard pricing element as published in a commercially or publicly available drug pricing database and a formula for reimbursement pricing, and populated according to the payer sheet defined by the Prescription Discount Administrator 1011. The benefit claim request is then submitted back to the Network Switch Computer 102 to be forwarded to the Prescription Discount Administrator 1011 for benefits consideration ("Claim One").

Upon approval of the benefits claim request, the Prescription Discount Administrator 1011 populates an approved claim response including, among other items, the dollar amount that will be paid to the submitting pharmacy and the remaining amount that is the responsibility of the prescription consumer and returns the approved claim response to the Network Switch Computer 102 for return to the submitting Pharmacy Computer 101.

Upon denial of the benefits claim request, the Prescription Discount Administrator 1011 populates a rejected claim response that details, among other things, the reason the claim was rejected and failed to produce an approved benefit claim response and returns the claim to the Network Switch Computer 102 for return to the Pharmacy Computer 101.

Upon receiving a denied claim response from the Prescription Discount Administrator 1011, the Network Switch Computer 102 identifies the claim as originating at the Benefits Aggregator Computer 103 and redirects the response to the Benefits Aggregator computer 103. The Benefits Aggregator Computer 103 consults the UPI Crosswalk File for determination of continuing in the process to the next benefit claim administrator or reversing any prior process and returning the rejected response to the Network Switch Computer 102 to be forwarded to the Pharmacy Computer 101.

Upon receiving an approved claim response from the Prescription Discount Administrator 1011, the Network Switch Computer 102 identifies the response claim as originating from the Benefits Aggregator Computer 103 and redirects the response to the Benefits Aggregator Computer 103. The Benefits Aggregator Computer 103, matches the response to the original benefit claim request, stores the benefits claim response and may extract from it any information necessary to populate an additional benefit claim request, consults the UPI Crosswalk File to identify further claim requests that need to occur, such as the Prescription Benefits Administrator 105, obtains other information necessary to populate the additional benefits claim request that is not present in the rebate administrator's response from the GEN Member ID file database or some other data source, creates a new claim request according to the payer sheet specified by the Prescription Benefits Administrator 105 and forwards the claim request to the Network Switch Computer 102 to be forwarded to the Manufacturer Rebate Administrator 104 for eligibility and benefits determination ("Claim Two"). The Manufacturer Rebate Administrator 104 may approve or deny the claim for benefits.

Upon denial of the benefits claim request, the Manufacturer Rebate Administrator 104 populates a rejected claim response that details, among other things, the reason the claim was rejected and failed to produce an approved benefit claim response and returns the claim to the Network Switch Computer 102 for return to the Pharmacy Computer 101.

Upon receiving a denied claim response from the Manufacturer Rebate Administrator 104, the Network Switch Computer 102 identifies the claim as originating at the Benefits Aggregator Computer 103 and redirects the response to the Benefits Aggregator computer 103. The Benefits Aggregator Computer 103 consults the UPI Crosswalk File, for determination of continuing in the process to the next benefit claim administrator or reversing any prior process and returning the rejected response to the Network Switch Computer 102 to be forwarded to the Pharmacy Computer 101.

Upon approval of the benefits claim request, the Manufacturer Rebate Administrator 104 populates an approved claim response including, among other items, the dollar amount that will be paid to the submitting pharmacy and the remaining amount that is the responsibility of the prescription consumer and returns the approved claim response to the Network Switch Computer 102 for return to the submitting Pharmacy Computer 101.

Upon receiving an approved claim response from the Manufacturer Rebate Administrator 104, the Network Switch Computer 102 identifies the claim as originating at the Benefits Aggregator Computer 103 and redirects the response to the Benefits Aggregator computer 103. The Benefits Aggregator 103 identifies the response claim as originating from the original benefit claim request, stores the benefits claim response and may extract from it any information necessary to populate an additional benefit claim request, obtains other information necessary to populate the additional benefits claim request that is not present in the rebate administrator's response from the Member ID file or some other data source, creates a new claim request according to the payer sheet specified by the Manufacturer Coupon Administrator 106 and forwards the claim request to the Network Switch Computer 102 for submission to the Manufacturer Coupon Administrator 106 for eligibility and benefits determination ("Claim Three"). The Manufacturer Coupon Administrator 106 may approve or deny the claim for benefits.

Upon receipt of the benefits claim request from the Network Switch Computer 102, the Manufacturer Coupon Administrator 106, may identify within the claim request one or more data elements which may include: From the HEADER segment: SERVICE PROVIDER ID QUALIFIER (FIELD 202-B2), SERVICE PROVIDER ID (FIELD 201-B1), DATE OF SERVICE (FIELD 401-D1), From the Claim Segment: PRODUCT/SERVICE ID QUALIFIER (FIELD 436-E1), PRODUCT/SERVICE ID (FIELD 407-D7), QUANTITY DISPENSED (FIELD 442-E7), COMPOUND CODE (FIELD 406-D6). From the various segments and data elements on the claim request as well as the instruction set sent to the manufacturer coupon administrator computer by the Benefits Aggregator 103, and the Member ID file, the Manufacturer Coupon Administrator 106 creates a query for approval to provide benefits for the product requested, in the amount requested, by the Pharmacy Computer 101 requesting it, at the time requested and submits the request to the Eligible Inventory Administrator 1010

The Eligible Inventory Administrator 1010 consults the database containing the data describing the available inventory remaining of that specific product, at the time requested, for the quantity requested at or associated with the SERVICE PROVIDER ID (FIELD 407-D7) or Pharmacy Computer 101 requesting it and provides an approved or denied response to the Manufacturer Coupon Administrator 106.

Upon receipt of a denied response to provide benefits based on remaining inventory from the Eligible Inventory Administrator 1010 by the Manufacturer Coupon Administrator 106, the Manufacturer Coupon Administrator 106 denies the benefit claim request and sends a rejected claim response to the Network Switch Computer 102 for return to the Pharmacy Computer 101 according to the payer sheet defined by the Manufacturer Coupon Administrator 106.

Upon receipt of an approved response to provide benefits based on remaining inventory from the Eligible Inventory Administrator 1010 by the Manufacturer Coupon Administrator 106, the Manufacturer Coupon Administrator 106 proceeds with the other rulesets that will determine the final approval or denial status of the claim request.

Upon denial of the benefits claim request, the Manufacturer Coupon Administrator 106 populates a rejected claim response that details, among other things, the reason the claim was rejected and failed to produce an approved benefit claim response and returns the claim to the Network Switch Computer 102 for return to the Pharmacy Computer 101.

Upon receiving a denied claim response from the Manufacturer Coupon Administrator 106, the Network Switch Computer 102 identifies the claim as originating at the Benefits Aggregator Computer 103 and redirects the response to the Benefits Aggregator computer 103. The Benefits Aggregator Computer 103 consults the UPI Crosswalk File, for determination of continuing in the process to the next benefit claim administrator or reversing any prior process and returning the rejected response to the Network Switch Computer 102 to be forwarded to the Pharmacy Computer 101.

Upon receiving an approved claim response from the Manufacturer Coupon Administrator 106, the Network Switch Computer 102 identifies the claim as originating at the Benefits Aggregator Computer 103 and redirects the response to the Benefits Aggregator computer 103. If no further available benefits are indicated in the Member ID file database or some other data source, Upon receipt of the benefits claim request from the Network Switch Computer 102, the Manufacturer Coupon Administrator 106, may identify within the claim request one or more data elements which may include: From the HEADER segment: SERVICE PROVIDER ID QUALIFIER (FIELD 202-B2), SERVICE PROVIDER ID (FIELD 201-B1), DATE OF SERVICE (FIELD 401-D1), From the Claim Segment: PRODUCT/SERVICE ID QUALIFIER (FIELD 436-E1), PRODUCT/SERVICE ID (FIELD 407-D7), QUANTITY DISPENSED (FIELD 442-E7), COMPOUND CODE (FIELD 406-D6). From the various segments and data elements on the claim request as well as the instruction set sent to the manufacturer coupon administrator computer by the Benefits Aggregator 103, and the Member ID file, the Manufacturer Coupon Administrator 106 creates a query for approval to provide benefits for the product requested, in the amount requested, by the Pharmacy Computer 101 requesting it, at the time requested and submits the request to the Eligible Inventory Administrator 1010.

The Eligible Inventory Administrator 1010 consults the database containing the data describing the available inventory remaining of that specific product, at the time requested, for the quantity requested at or associated with the SERVICE PROVIDER ID (FIELD 407-D7) or Pharmacy Computer 101 requesting it and provides an approved or denied response to the Manufacturer Coupon Administrator 106.

Upon receipt of a denied response to provide benefits based on remaining inventory from the Eligible Inventory Administrator 1010 by the Manufacturer Coupon Administrator 106, the Manufacturer Coupon Administrator 106 denies the benefit claim request and sends a rejected claim response to the Network Switch Computer 102 for return to the Pharmacy Computer 101 according to the payer sheet defined by the Manufacturer Coupon Administrator 106.

Upon receipt of an approved response to provide benefits based on remaining inventory from the Eligible Inventory Administrator 1010 by the Manufacturer Coupon Administrator 106, the Manufacturer Coupon Administrator 106 proceeds with the other rulesets that will determine the final approval or denial status of the claim request.

Upon approval of the benefits claim response, the Manufacturer Coupon Administrator 106 populates a benefit claim response that details, among other things, the dollar amount that will be paid to the original submitting pharmacy and the amount to be collected from the prescription consumer and returns the claim to the Network Switch Computer 102 for return to the Pharmacy Computer 101.

Upon denial of the benefits claim request, the Manufacturer Coupon Administrator 106 populates a rejected claim response that details, among other things, the reason the claim was rejected and failed to produce an approved benefit claim response and returns the claim to the Network Switch Computer 102 for return to the Pharmacy Computer 101.

Upon receiving a denied claim response from the Manufacturer Coupon Administrator 106, the Network Switch Computer 102 identifies the claim as originating at the Benefits Aggregator Computer 103 and redirects the response to the Benefits Aggregator computer 103. The Benefits Aggregator Computer 103 consults the UPI Crosswalk File, for determination of continuing in the process to the next benefit claim administrator or reversing any prior process and returning the rejected response to the Network Switch Computer 102 to be forwarded to the Pharmacy Computer 101.

Upon receiving an approved claim response from the Manufacturer Coupon Administrator 106, the Network Switch Computer 102 identifies the response claim as originating from the Benefits Aggregator Computer 103, and redirects the response to the Benefits Aggregator computer 103. The Benefits Aggregator 103 identifies the response claim as originating from the original benefit claim request, stores the benefits claim response and may extract from it any information necessary to populate an additional benefit claim request, obtains other information necessary to populate the additional benefits claim request that is not present in the rebate administrator's response from the UPI Crosswalk File database or other data source, creates a new claim request according to the payer sheet specified by the WHSE Coupon Administrator 107 ("Claim Four") and forwards the claim request to the WHSE Coupon Administrator 107 for eligibility and benefits determination. The WHSE Coupon Administrator 107 may approve or deny the claim for benefits. If no further available benefits are indicated in the Member ID file database or some other data source, the (manufacturer coupon administrator 106 or WHSE Coupon Administrator 107) returns the claim to the Network Switch Computer 102 for return to the Pharmacy Computer 101).

Upon receipt of the benefits claim request from the Network Switch Computer 102, the WHSE Coupon Administrator 107, may identify within the claim request one or more data elements which may include: From the HEADER segment: SERVICE PROVIDER ID QUALIFIER (FIELD 202-B2), SERVICE PROVIDER ID (FIELD 201-B1), DATE OF SERVICE (FIELD 401-D1), From the Claim Segment: PRODUCT/SERVICE ID QUALIFIER (FIELD 436-E1), PRODUCT/SERVICE ID (FIELD 407-D7), QUANTITY DISPENSED (FIELD 442-E7), COMPOUND CODE (FIELD 406-D6). From the various segments and data elements on the claim request as well as the instruction set sent to the WHSE Coupon Administrator 107 by the Benefits Aggregator 103, and the Member ID file, the WHSE Coupon Administrator 107 creates a query for approval to provide benefits for the product requested, in the amount requested, by the Pharmacy Computer 101 requesting it, at the time requested and submits the request to the Eligible Inventory Administrator 1010.

The Eligible Inventory Administrator 1010 consults the database containing the data describing the available inventory remaining of that specific product, at the time requested, for the quantity requested at or associated with the SERVICE PROVIDER ID (FIELD 407-D7) or Pharmacy Computer 101 requesting it and provides an approved or denied response to the WHSE Coupon Administrator 107.

Upon receipt of a denied response to provide benefits based on remaining inventory from the Eligible Inventory Administrator 1010 by the WHSE Coupon Administrator 107, the WHSE Coupon Administrator 107 denies the benefit claim request and sends a rejected claim response to the Network Switch Computer 102 for return to the Pharmacy Computer 101 according to the payer sheet defined by the WHSE Coupon Administrator 107.

Upon receipt of an approved response to provide benefits based on remaining inventory from the Eligible Inventory Administrator 1010 by the WHSE Coupon Administrator 107, the WHSE Coupon Administrator 107 proceeds with the other rulesets that will determine the final approval or denial status of the claim request.

Upon approval of the benefits claim request, the WHSE Coupon Administrator 107 populates a benefit claim response that details, among other things, the dollar amount that will be paid to the original submitting pharmacy and the amount to be collected from the prescription consumer and returns the claim to the Network Switch Computer 102 for return to the Pharmacy Computer 101.

Upon denial of the benefits claim request, the WHSE Coupon Administrator 107 populates a rejected claim response that details, among other things, the reason the claim was rejected and failed to produce an approved benefit claim response and returns the claim to the Network Switch Computer 102 for return to the Pharmacy Computer 101.

Upon receiving a denied claim response from the WHSE Coupon Administrator 107, the Network Switch Computer 102 identifies the claim as originating at the Benefits Aggregator Computer 103 and redirects the response to the Benefits Aggregator computer 103. The Benefits Aggregator Computer 103 consults the UPI Crosswalk File, for determination of continuing in the process to the next benefit claim administrator or reversing any prior process and returning the rejected response to the Network Switch Computer 102 to be forwarded to the Pharmacy Computer 101.

Upon receiving an approved claim response from the WHSE Coupon Administrator 107, the Network Switch Computer 102 identifies the response claim as originating from the Benefits Aggregator Computer 103 and redirects the response to the Benefits Aggregator computer 103. The Benefits Aggregator 103 identifies the response claim as originating from the original benefit claim request, stores the benefits claim response and may extract from it any information necessary to populate an additional benefit claim request, obtains other information necessary to populate the additional benefits claim request that is not present in the rebate administrator's response from the UPI Crosswalk File database or other data source.

If no further available benefits are indicated in the UPI Crosswalk File database or some other data source, the Benefits Aggregator 103 aggregates the sum of the payable amounts indicated on each approved claim response from the various benefits administration computers, populates the sum amount and the final amount due from the prescription consumer into a response to the original claim request, and returns the approved claim response to the Network Switch Computer 102 for return to the Pharmacy Computer 101.

The Pharmacy collects the final amount owed by the prescription consumer and provides the fulfilled prescription order to the prescription consumer.

The Network Switch Computer 102 or the Benefits Aggregator 103 then creates a data file that identifies the aggregated claim from all others and also contains each individual benefit claim response from each of the Rebate Administrator 104 (herein "Claim One"), Prescription Benefits Administrator 105 (herein "Claim Two"), Manufacturer Coupon Administrator 106 (herein "Claim Three"), and the WHSE Coupon Administrator 107 (herein "Claim Four"). This data file will be utilized by the pharmacy or an entity acting on behalf of the pharmacy to reconcile payments as they arrive to the individual claims that occurred as a result of the original claim request. Either the Benefits Aggregator 103 or the individual benefits administrator computers (104, 106, 107, 1010, 1011) will create and send documentation along with the payment for approved claims to the Pharmacy Computer 101 or the Prescription Consumer 100 for identification of the individual claims or inquiries that were processed as a part of the aggregated response and the level of benefit that was provided as part of the aggregated response.

Each of the claim responses may also be communicated to one or more of any of the benefits administrators as informational data concerning the claim in which that benefit administrator was involved in providing a financial benefit to the prescription consumer for at least a portion of the cost of the prescription.

It should be noted that each claim request that is created along with the transmission, processing, response, sequencing, subsequent claim creation, transmission, processing, response, continuing until no additional claims need be created in association with the original claim request, the final aggregated claim response creation and return to the pharmacy must occur within the time that the connection with the pharmacy for the original request is still open; usually less than fifteen seconds.

Figure 6A:
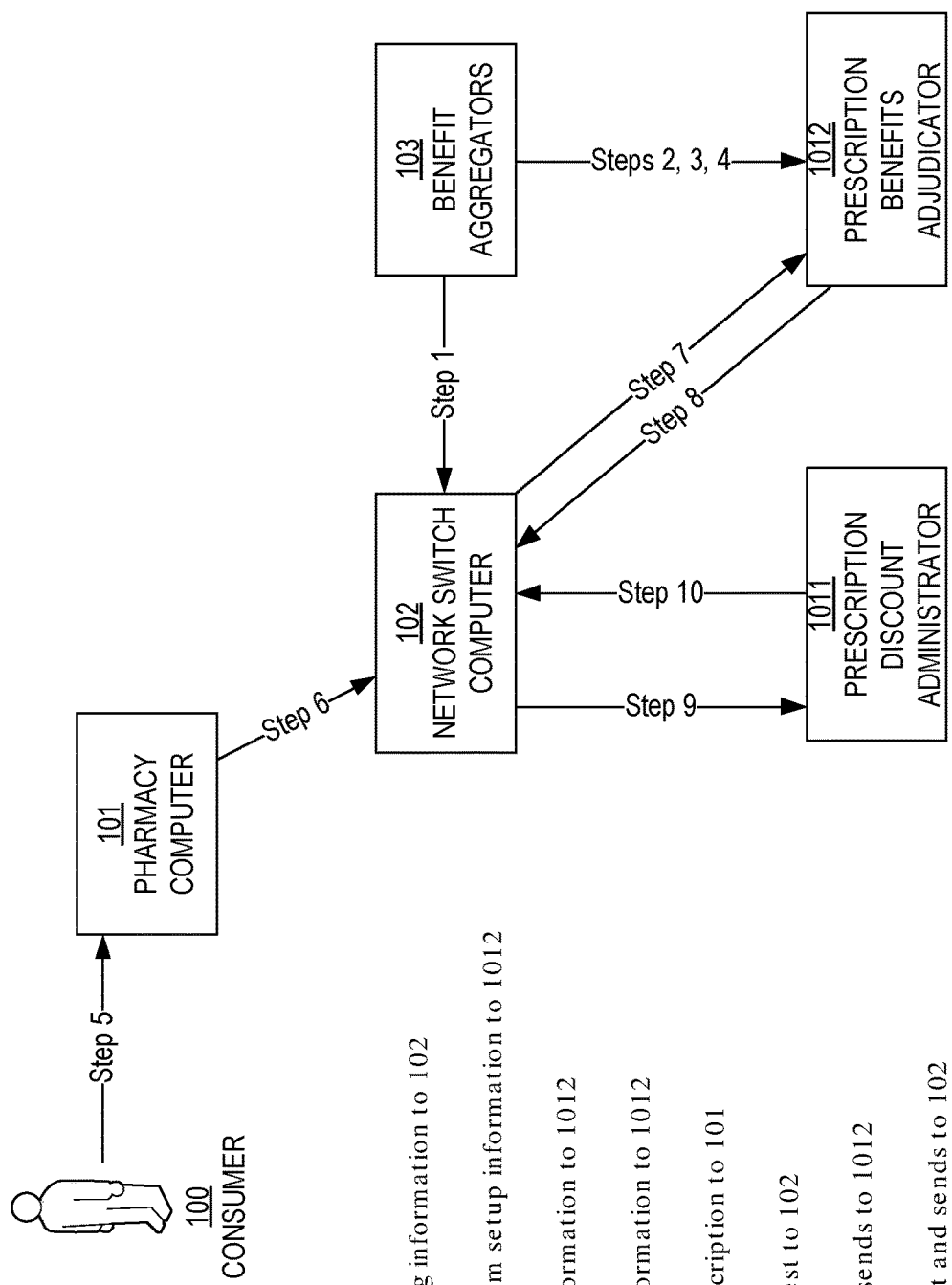
Figure 6B:
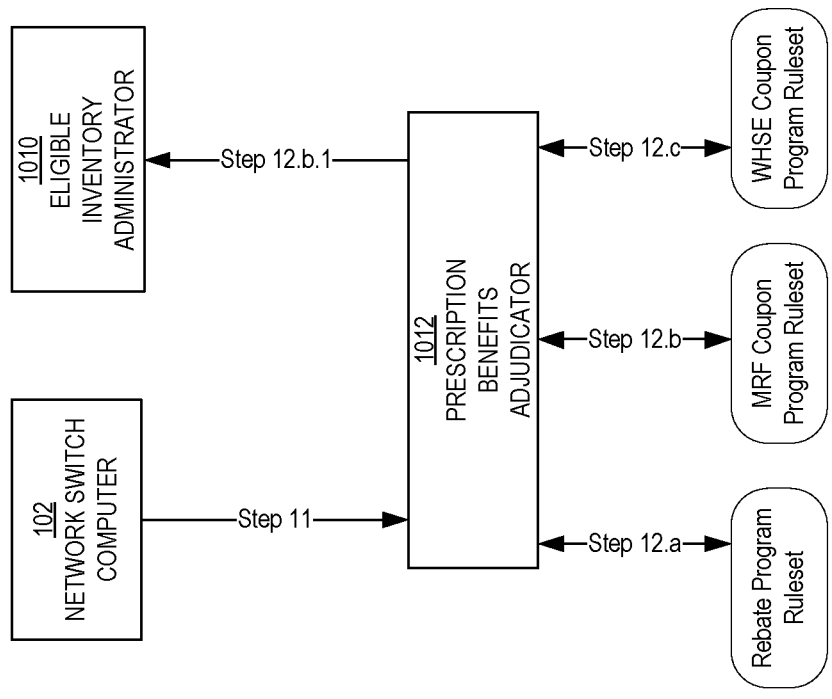
Figure 7A:
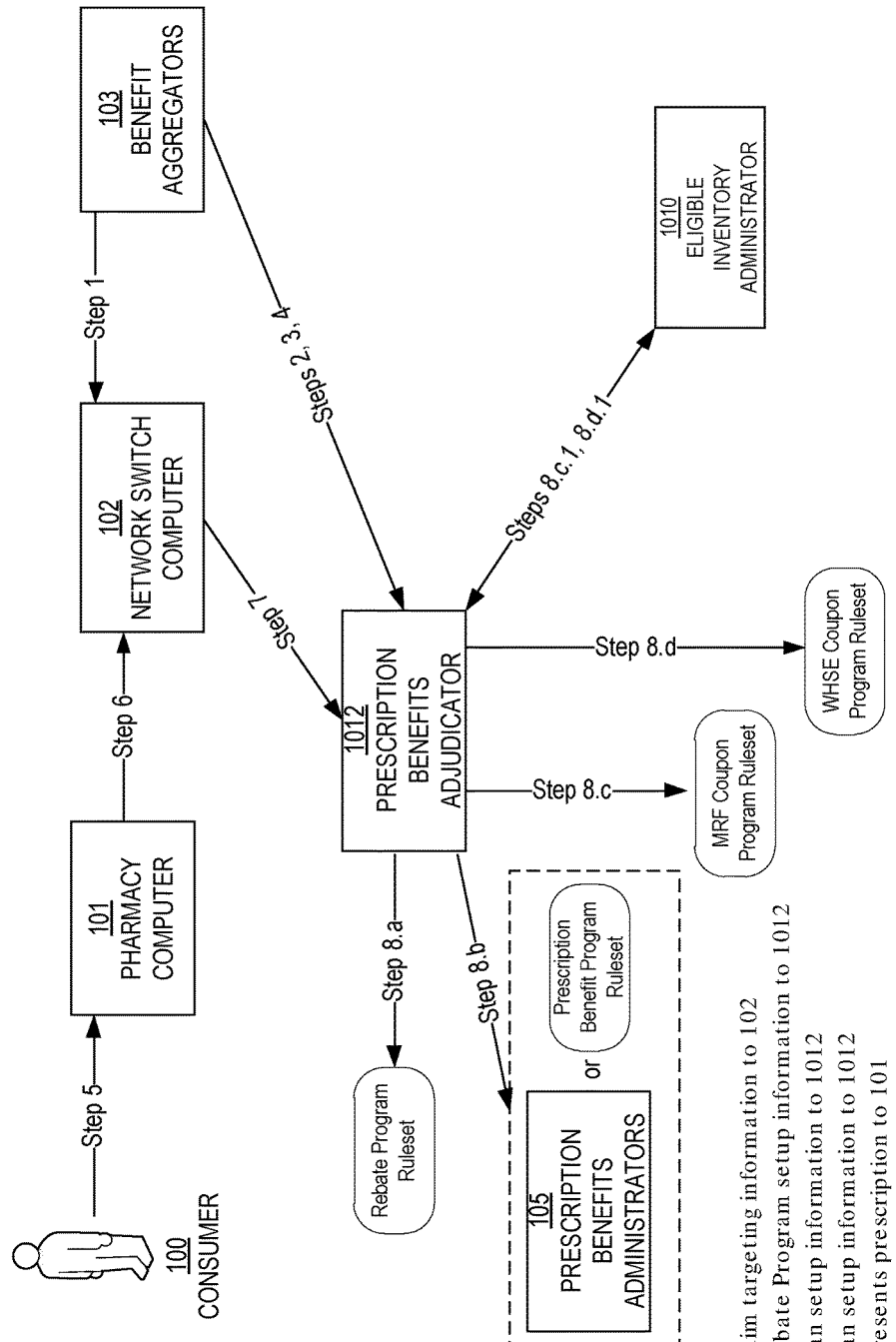
FIGS. 7A and 7B show an example embodiment of the invention in which a prescription consumer with insurance coverage presents a prescription order to the pharmacy or dispensing prescriber to be fulfilled.
Figure 7B:
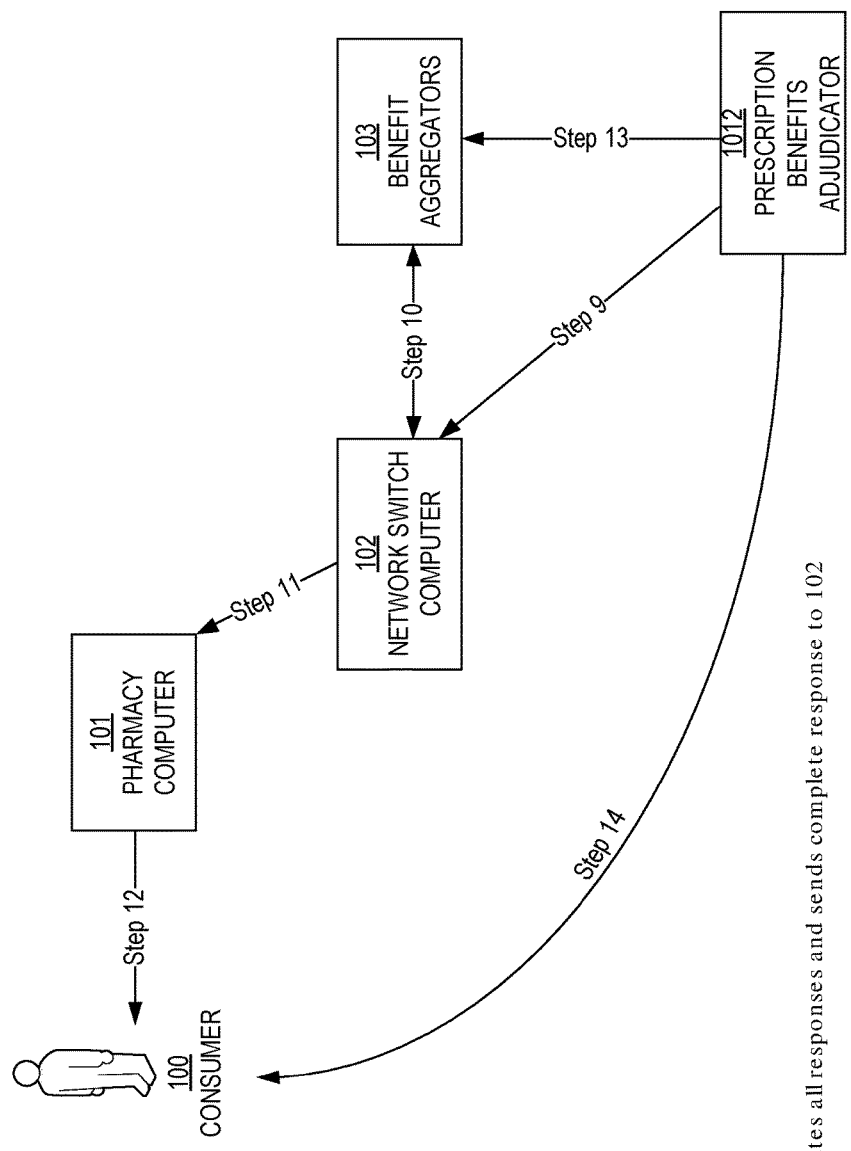
Figure 8A:
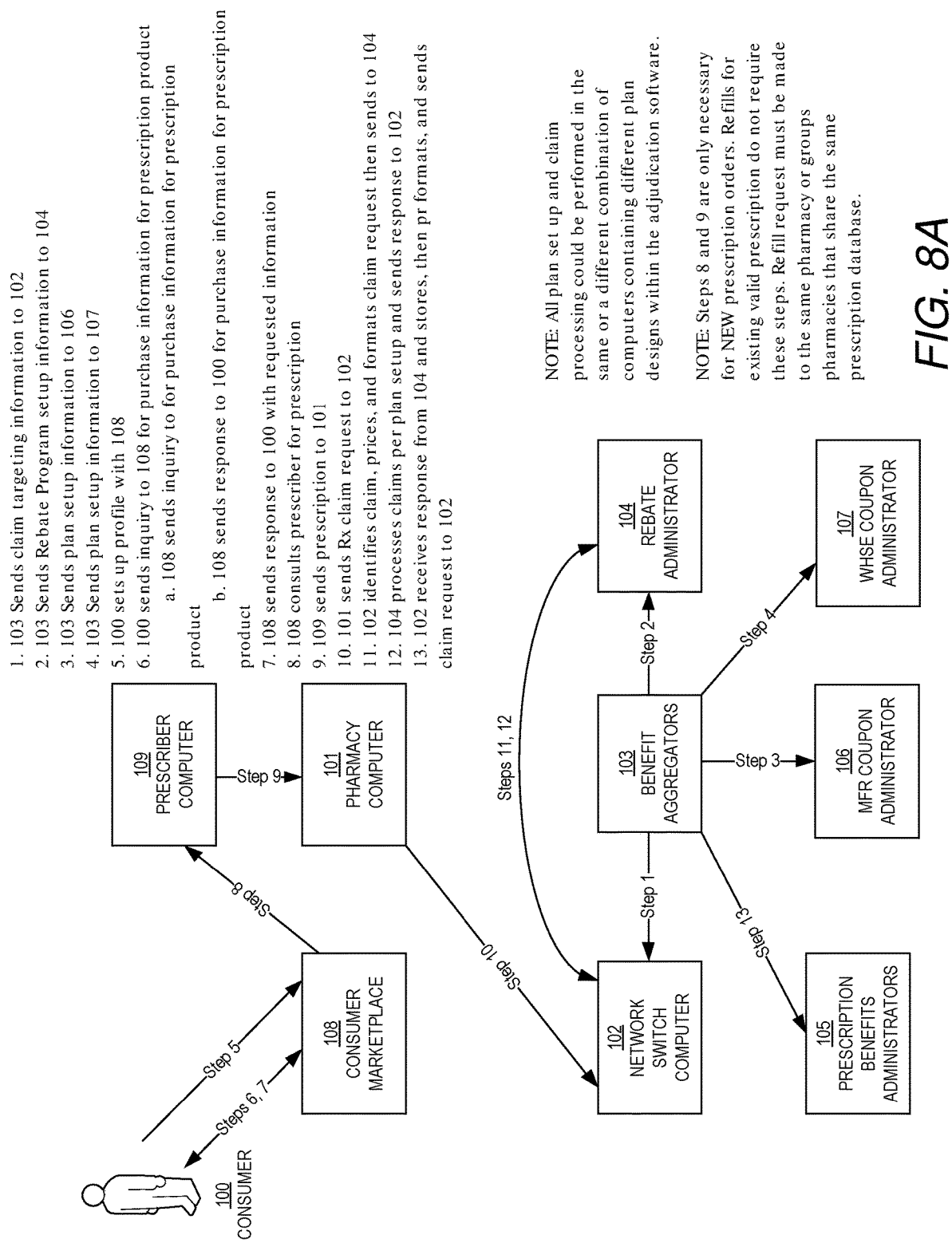
FIGS. 8A and 8B show an example embodiment in which a prescription consumer with insurance coverage submits an inquiry to a consumer marketplace requesting information about any participating Healthcare Provider (HCP) that may be able and willing to fulfil the prescription order.
Figure 8B:
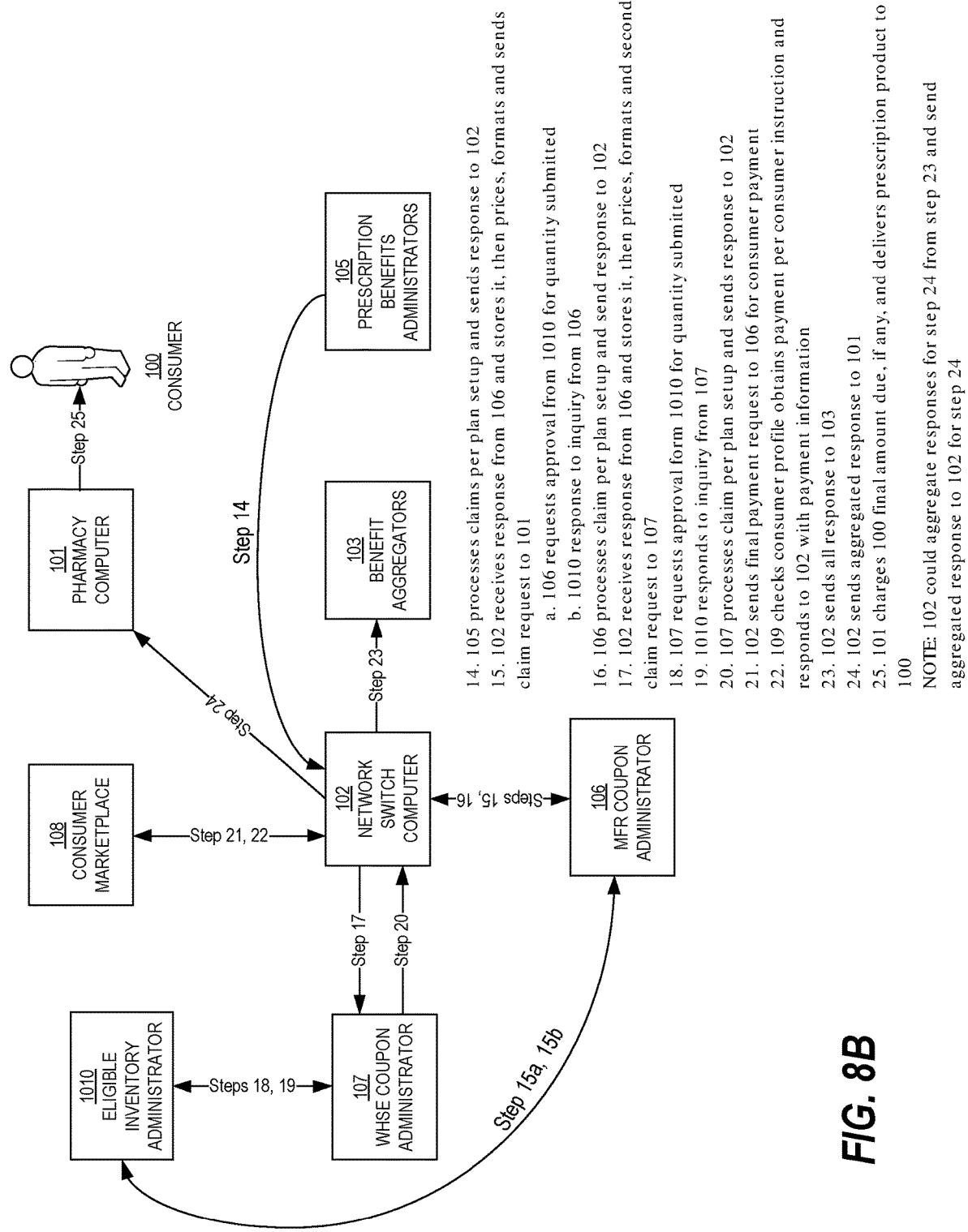
Figure 9A:
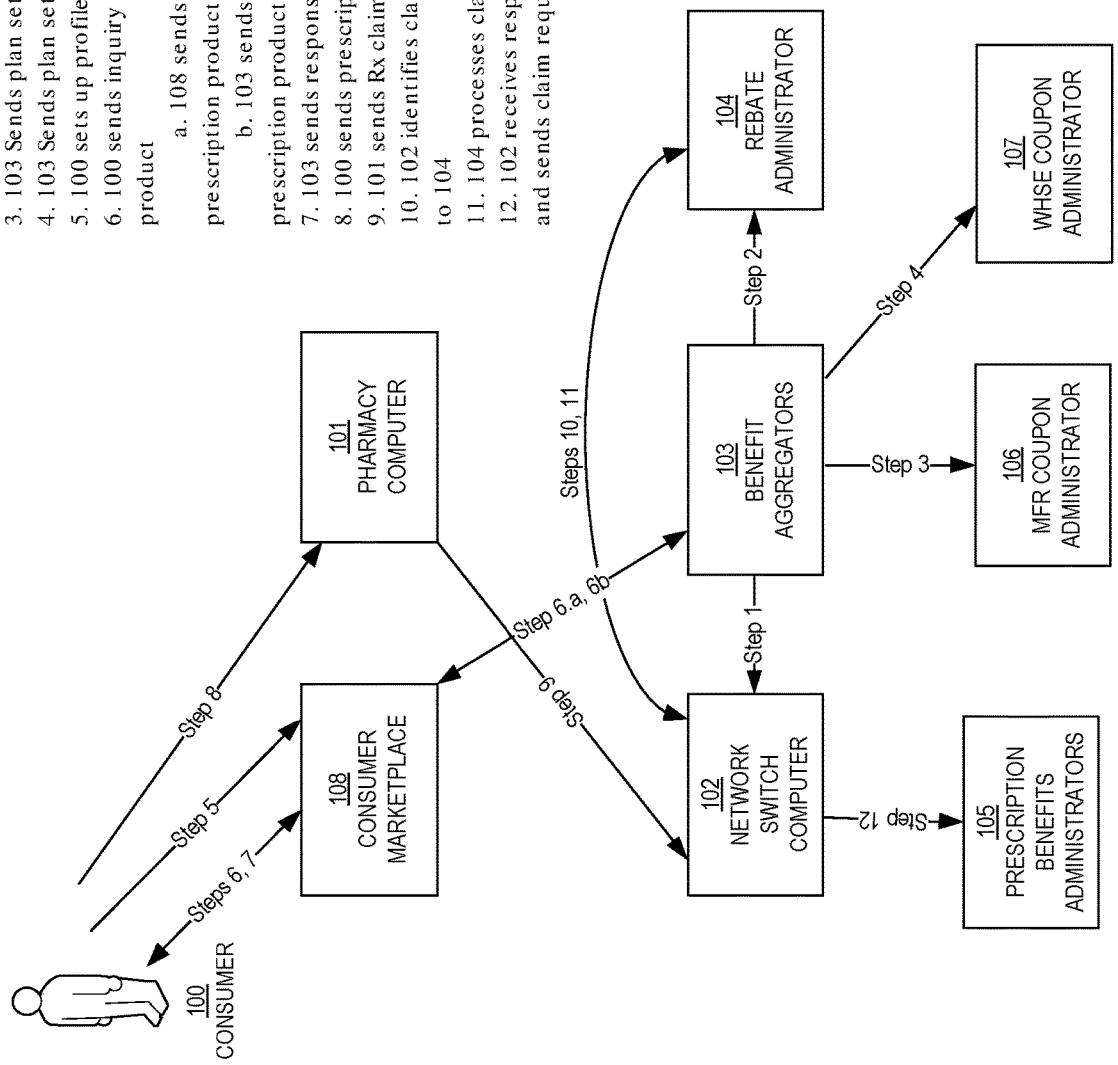
FIGS. 9A and 9B show an example embodiment in which a prescription consumer with insurance coverage submits an inquiry to a consumer marketplace requesting information about any participating HCP that may be able and willing to fulfil the prescription order.
Figure 9B:
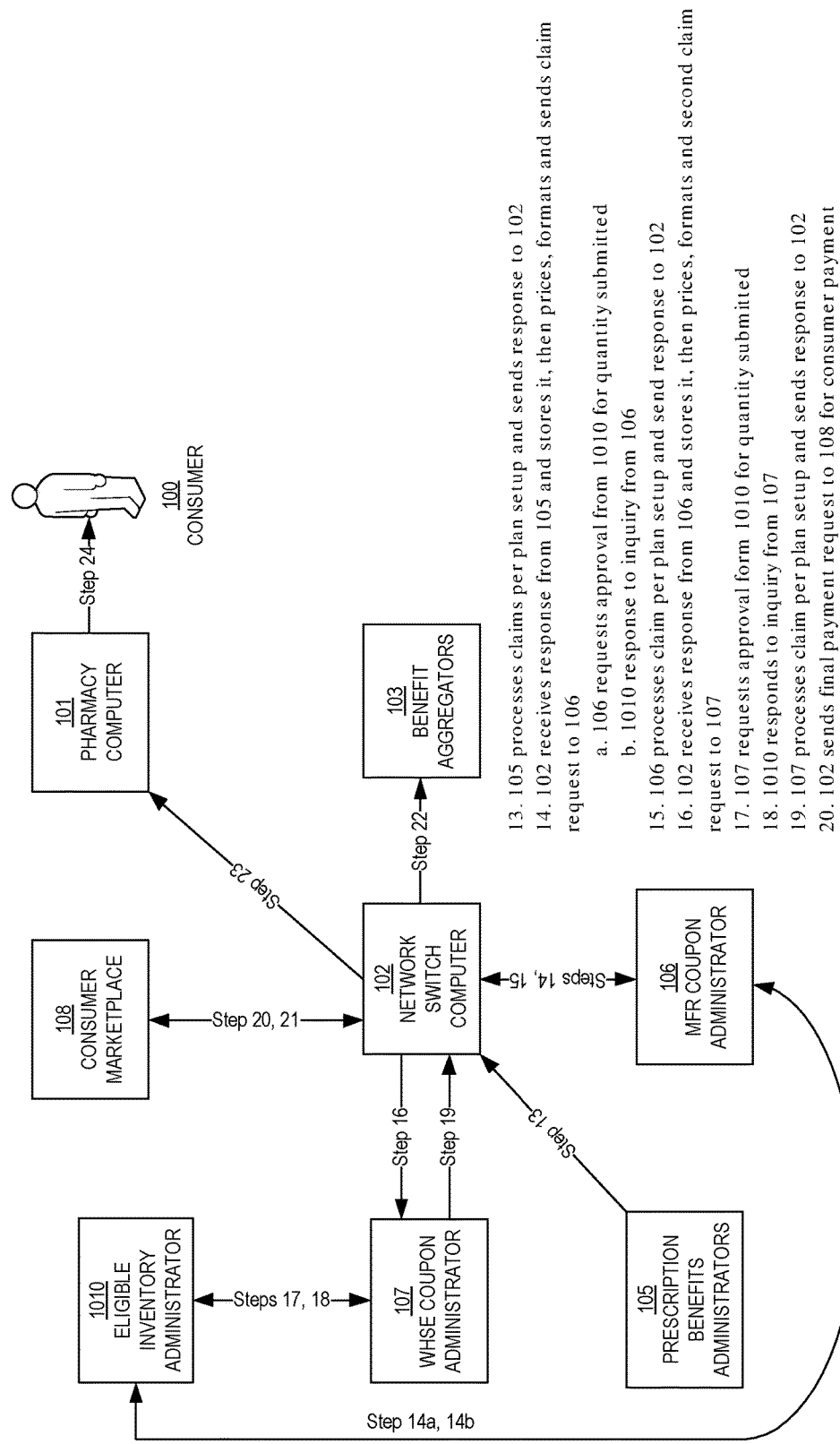
Figure 10A:
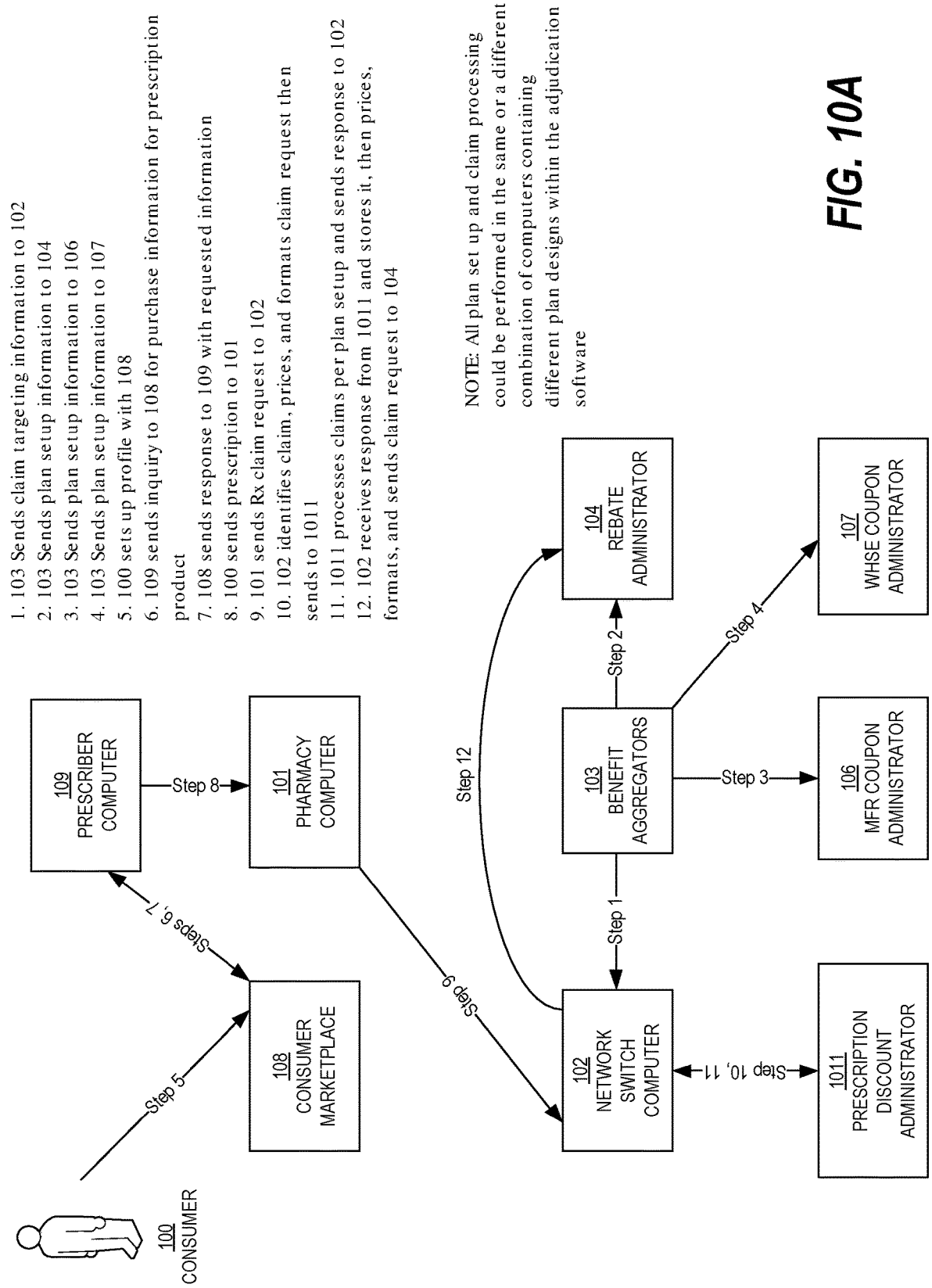
FIGS. 10A and 10B show an example embodiment where a prescriber request is processed with an uninsured market
Figure 10B:
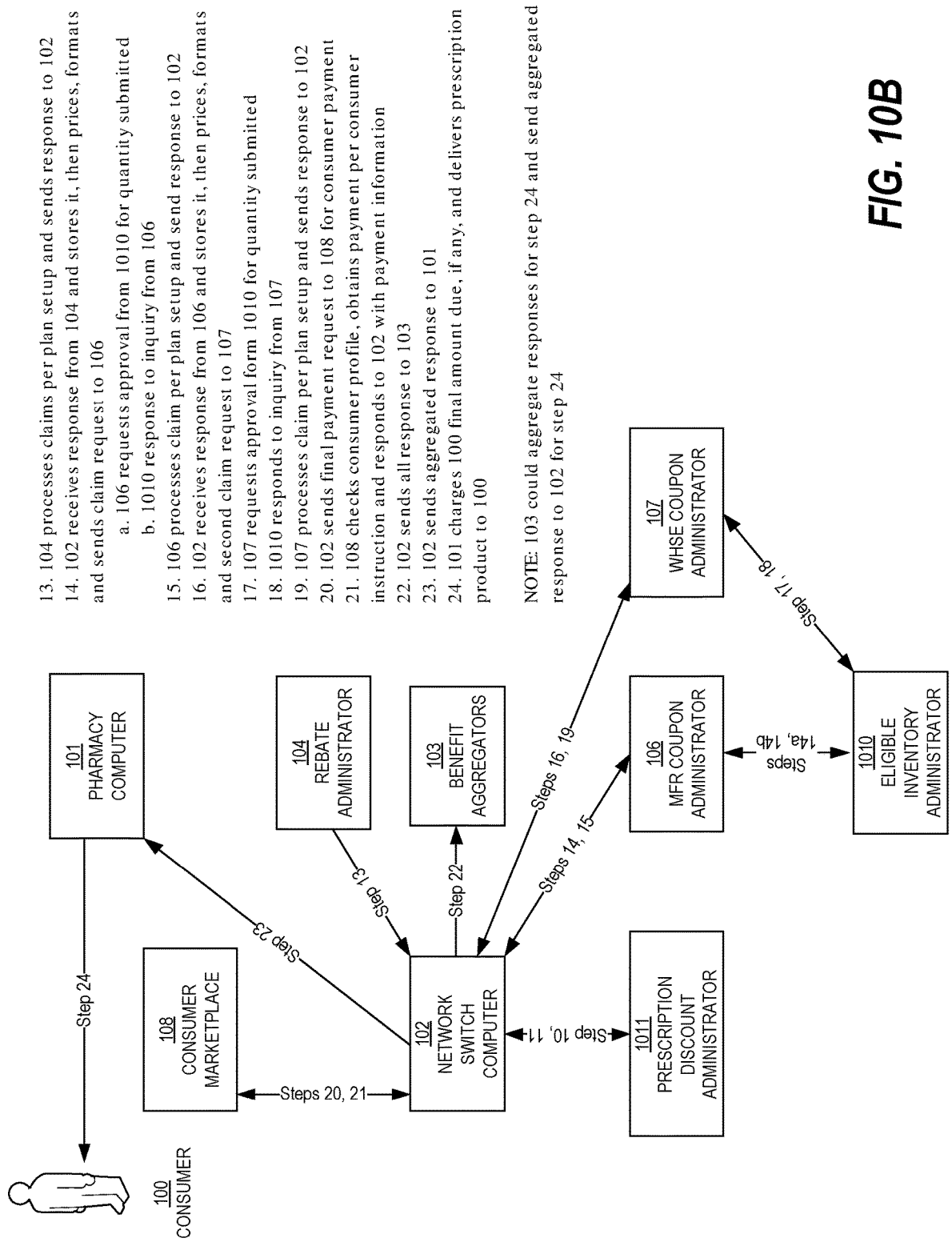
Figure 11A:
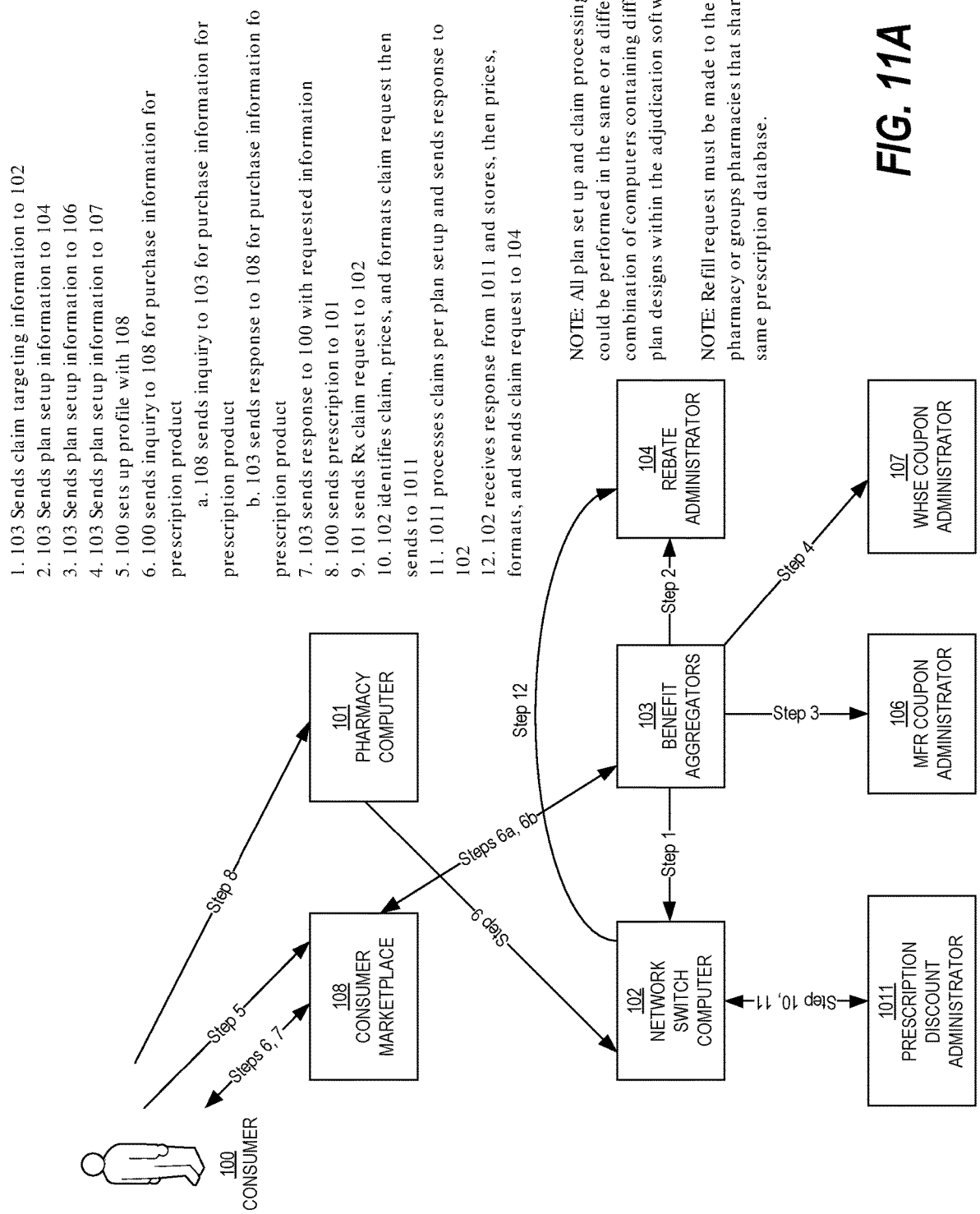
FIGS. 11A and 11B show an example embodiment where a refill prescription request is processed with an uninsured market
Figure 11B:
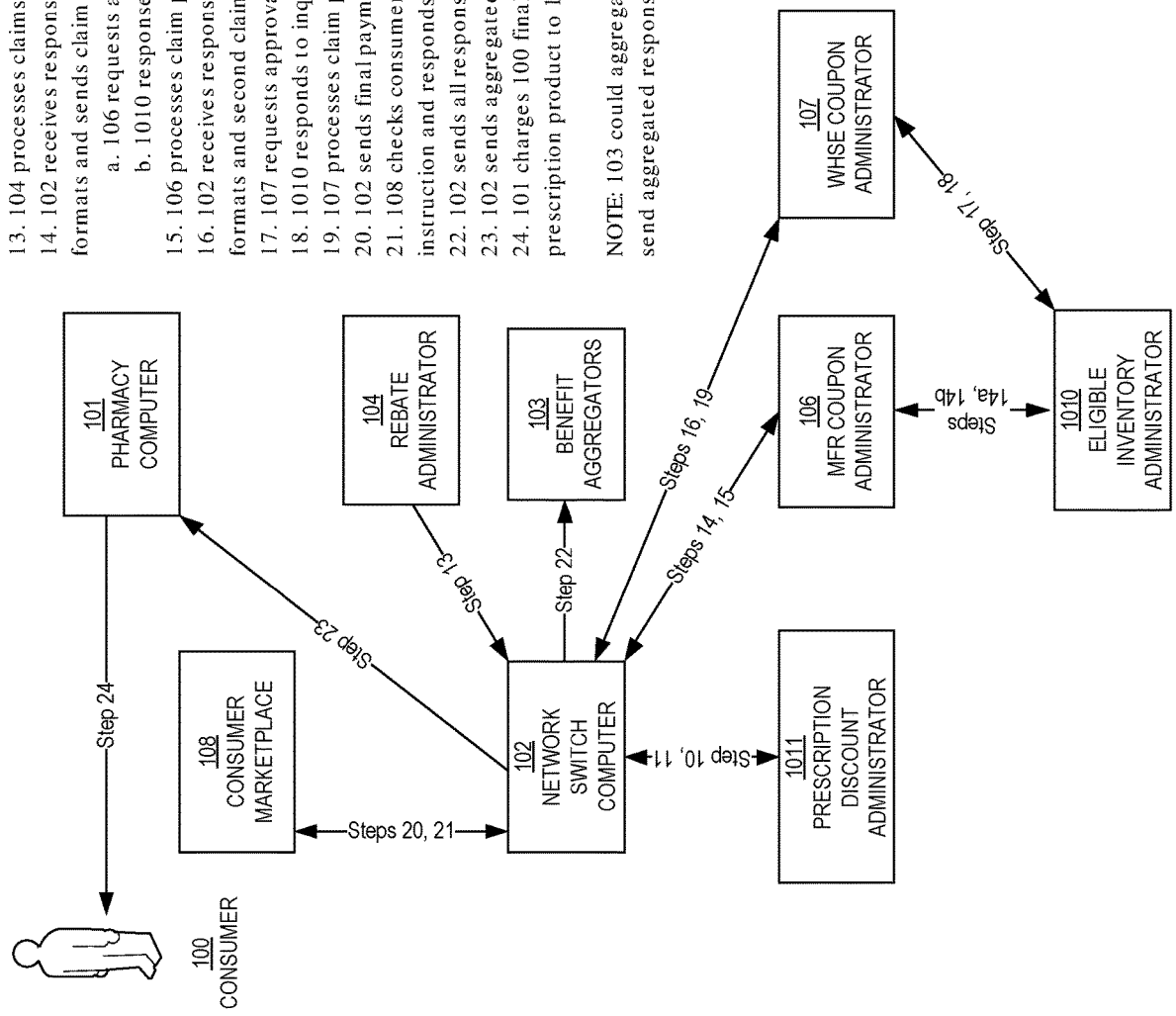
Figure 12A:
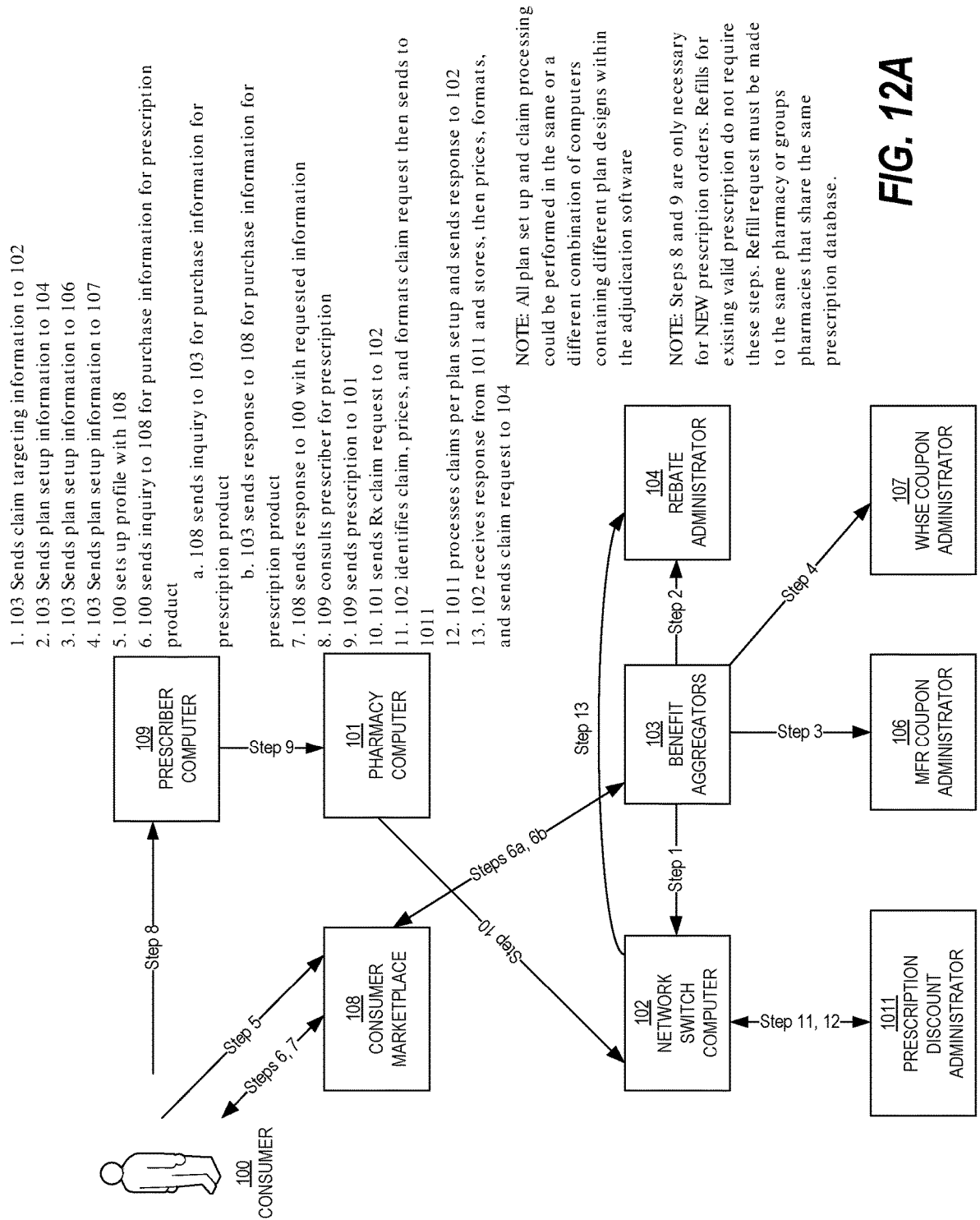
FIGS. 12A and 12B show an example embodiment where a new prescription request is processed with an uninsured market.
Figure 12B:
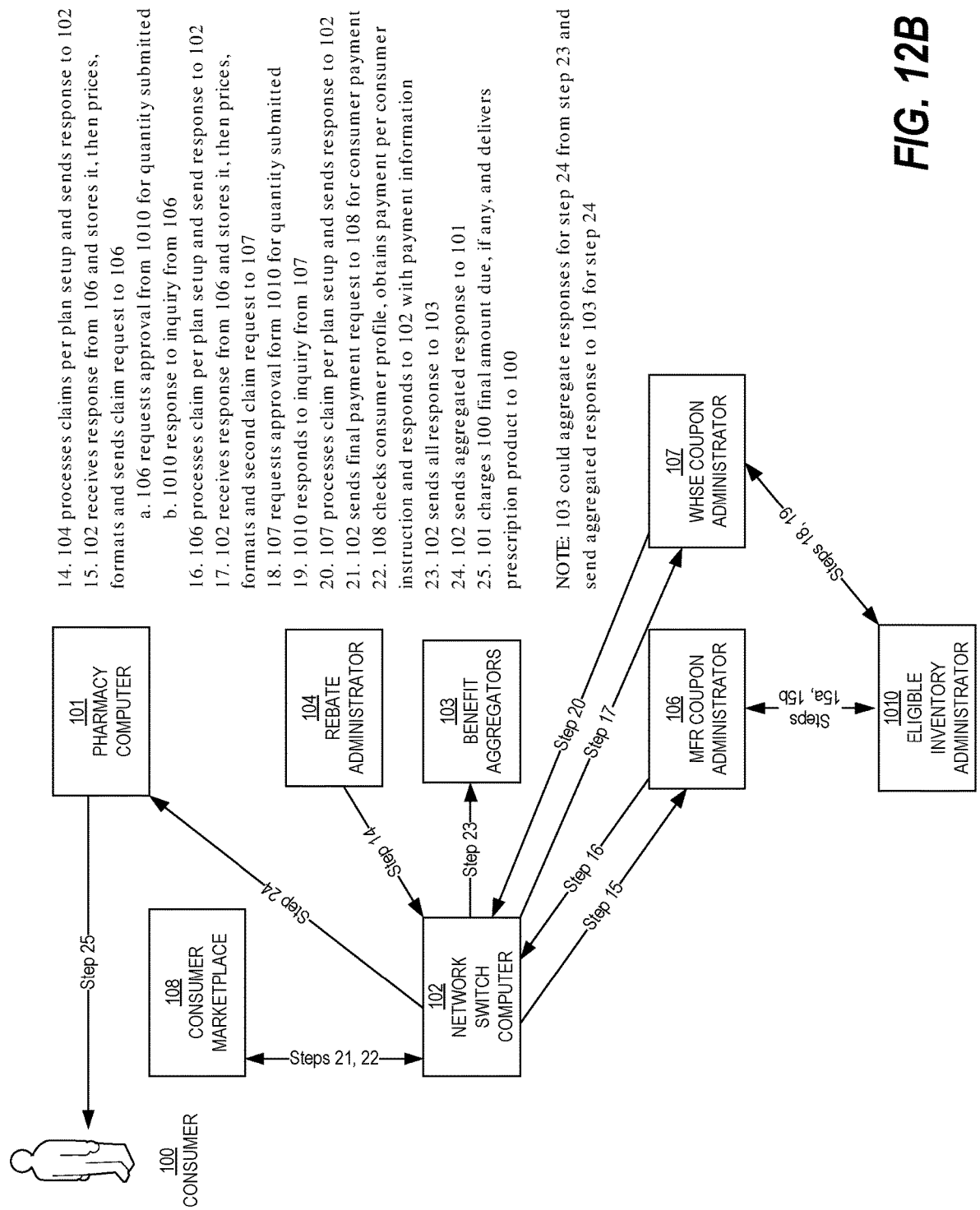

FIGS. 6A-6C show an example embodiment of the invention in which a prescription consumer with insurance coverage, either him/herself or an entity acting on the prescription consumer's behalf such as an electronic prescription communication service presents a prescription order to the pharmacy or dispensing prescriber to be fulfilled. Each step represents an action performed at that location and the submission of the claim to the next entity in the continuum to the end of the description. If any of the steps fail to result in an approved response or completed action, the other steps in the continuum may either continue or the process may proceed in reverse order to the originator with a message being provided to the HCP to make corrections to the submission request or for provision to the prescription consumer as to why the prescription benefit claim request was not successful; one example is as follows: (a) steps 1 through 12.*a* are successful; (b) step 12.*b* fails due to the prescription consumer's insurance benefit being expired; (c) step 12.*a* is reversed; (d) computer Prescription Benefits Adjudicator 1012 sends reject message from step 12.*b* to the Network Switch Computer 102 for return to the Pharmacy Computer 101; and (e) the Pharmacy Computer 101 is provided with a message advising the prescription consumer of the unavailability of prescription benefits due to expired coverage.

In the example of FIGS. 6A-6C, the Benefits Aggregator 103 may be engaged by one or more benefits administrator computers 104, 105, 106, 107, 1011 to provide aggregation, sequencing, and/or administration services for prescription consumers that may be beneficiaries of the benefits provided by that entity. The prescription benefit providers may supply to the benefits aggregator a means of identifying prescription consumers that may be eligible to receive benefits. In addition, the prescription benefit provider may provide to the benefits aggregator the rulesets that determine if the prescription claim or inquiry request and the associated product and prescription consumer is eligible to receive benefits and what level of benefits are to be provided if eligible. The Benefits Aggregator 103 supplies various information to the Prescription Benefits Adjudicator 1012 and to the Network Switch Computer 102 (it should be understood by one skilled in the art that there could be a plurality of the entity fitting the description) to facilitate the identification of potentially eligible inquiries or claims requests for entry into the aggregated prescription benefits program. The Benefits Aggregator 103 or other entity performing program administration services for the benefits administrator computers (104, 105, 106, 107, 1011 as shown in FIG. 1) sets up program design details in the Prescription Benefits Adjudicator 1012 computers in order to complete the successful administration of prescription benefit claim or inquiry requests. The Pharmacy Computer 101 receives a prescription order from or on the behalf of a Prescription Consumer 100 whether from manual data entry by a human or machine or transmitted in electronic form over some communication interface such as an electronic prescription network. The Pharmacy Computer 101 formats the prescription order into an electronic benefit claim request defined by a rebate Program Ruleset in the form of a payer sheet and adjudicates the claim appropriately.

Continuing with reference to FIGS. 6A-6C, the Pharmacy Computer 101 receives a prescription order from or on the behalf of a Prescription Consumer 100 whether from manual data entry by a human or machine or transmitted in electronic form over some communication interface such as an electronic prescription network. The Pharmacy Computer 101 formats the prescription order into an electronic benefit claim request defined by a Prescription Discount Administrator 1011 in the form of a payer sheet and submits it to the Network Switch Computer 102 to have the data contained therein checked for accuracy and appropriateness and to utilize the Network Switch Computer 102 connection to one or more of the various benefits administrator computers (104, 105, 106, 107, 1011, 1012). The Network Switch Computer 102 interrogates the electronic benefit claim request for identifying characteristics that are provided to the Network Switch Computer 102 from the Benefits Aggregator 103 by means of a data file, internal database, or remote connection to an external database. If the electronic benefit claim request meets the requirements of identification, it is then targeted for further action. The Network Switch Computer 102 contains a listing of instructions relating to the benefits that may be available for the electronic benefit claim request and the order in which one or more requests must be made to one or more benefit administrator(s). In the example of FIGS. 6A and 6B, it is understood that the claim must first be formatted as a primary claim request containing data that is obtained from the Member ID file or some other data source and populated according to the payer sheet defined by the Prescription Discount Administrator 1011 if that is not already the case when submitted by the Pharmacy Computer 101. The benefit claim request is then submitted to the Prescription Benefits Adjudicator 1012 for benefits consideration (Claim One).

Upon receiving a claims request from the Network Switch Computer 102, the Prescription Benefits Adjudicator 1012 identifies the request being designated for the Prescription Discount Administrator 1011 or ruleset and adjudicates the claim appropriately. The claim is adjudicated internally by considering the prescription discount program ruleset; the adjudication may result in an approved or denied response.

Upon receiving an approved response the Prescription Benefits Adjudicator 1012 identifies the response as originating from the original benefit claim request, stores the benefits claim response and may extract from it any information necessary to populate the additional benefits claim request that is not present in the Prescription Discount Administrator computer's 1011 response from the Member ID file database or other data source, creates a new claim request according to the payer sheet specified by the Rebate program Ruleset and adjudicates the claim appropriately. The claim is adjudicated internally by considering the Rebate program ruleset; the adjudication may result in an approved or denied response.

Upon approval of the benefits claim request, the Rebate Program Ruleset populates a benefit claim response that details, among other things, the dollar amount that will be paid to the original submitting pharmacy and the amount to be collected from the prescription consumer and creates a response output for the Prescription Benefits Adjudicator 1012 for return to the Pharmacy Computer 101.

Upon receiving an approved response from the Rebate Program Ruleset, the Prescription Benefits Adjudicator 1012 stores the benefits claim response and may extract from it the information necessary to populate an additional benefit claim request for the Manufacturer Coupon Program Ruleset. Other information necessary to populate the additional benefits claim request that is not present in the first benefits claim response is obtained from the Member ID file database or other data source. The Prescription Benefits Adjudicator 1012 then completes the creation of the additional benefits claim request according to the payer sheet for the Manufacturer Coupon Program Ruleset and adjudicates the claim appropriately. During the determination of eligibility and level of benefits to be provided, the Prescription Benefits Adjudicator 1012 may request from the Eligible Inventory Administrator 1010 approval to dispense inventory for which there is benefits available.

Upon approval to dispense the inventory with applied benefit, the Manufacturer Coupon Program Ruleset continues with its benefits eligibility and level determination. The Manufacturer Coupon Program Ruleset may approve or deny the claim for benefits.

Upon approval of the benefits claim request, the Manufacturer Coupon Program Ruleset populates a benefit claim response that details, among other things, the dollar amount that will be paid to the original submitting pharmacy and the amount to be collected from the prescription consumer and creates a response output for the Prescription Benefits Adjudicator 1012 for return to the Pharmacy Computer 101.

Upon receiving an approved response from the manufacturer coupon program ruleset, the Prescription Benefits Adjudicator 1012 identifies the response claim as originating from the additional benefit claim request, stores the benefits claim response and extracts from it the information necessary to populate an additional benefit claim request for the WHSE Coupon Program Ruleset. Other information necessary to populate the additional benefits claim request that is not present in the first benefits claim response is obtained from the Member ID file database or other data source. The Prescription Benefits Adjudicator 1012 then completes the creation of the additional benefits claim request according to the payer sheet for the WHSE coupon Program Ruleset and adjudicates the claim properly. During the determination of eligibility and level of benefits to be provided, the Prescription Benefits Adjudicator 1012 may request approval from the Eligible Inventory Administrator 1010 for approval to dispense inventory for which there is benefits available.

Upon approval to dispense the inventory with applied benefit, the WHSE Coupon Program Ruleset continues with its benefits eligibility and level determination. The WHSE coupon program ruleset may approve or deny the claim for benefits. Upon approval of the benefits claim request, the WHSE Coupon Administrator 107 populates a benefit claim response that details, among other things, the dollar amount that will be paid to the original submitting pharmacy and the amount to be collected from the prescription consumer and returns the claim to the Prescription Benefits Adjudicator 1012 for return to the Pharmacy Computer 101. The Prescription Benefits Adjudicator 1012 identifies the response claim as originating from the additional benefit claim request and withdraws the amounts owed to the pharmacy for each of the approved claims. The amounts are then aggregated, and a claim response is constructed for the original benefit claim request and the total amount owed by the group of benefits administrators and rulesets is populated into the benefit claim response along with the final amount owed by the prescription consumer as populated in the fourth benefit claim response. The aggregated benefit claim response is then forwarded to the Pharmacy Computer 101 as a response to the original claim request. The pharmacy collects the final amount owed by the Prescription Consumer 100 and provides the fulfilled prescription order to the Prescription Consumer 100.

The Prescription Benefits Adjudicator 1012 or the Network Switch Computer 102 then creates a data file that identifies the aggregated claim from all others and also contains each individual benefit claim response from each of the Prescription Discount Administrator 1011 (Claim One), Rebate Administrator 104 (Claim Two), Manufacturer Coupon Administrator 106 (Claim Three), and the WHSE Coupon Administrator 107 (Claim Four). This data file will be utilized by the pharmacy or an entity acting on behalf of the pharmacy to reconcile payments as they arrive to the individual claims that occurred as a result of the original claim request. Either the Benefits Aggregator 103 or the individual benefits administrator computers (104, 105, 106, 107) will create and send documentation along with the payment for approved claims to the pharmacy, Pharmacy Computer 101, or the Prescription Consumer 100 for identification of the individual claims or inquiries that were processed as a part of the aggregated response and the level of benefit that was provided as part of the aggregated response.

In some embodiments, the Benefits Aggregator 103, the Network Switch Computer 102, or the Prescription Benefits Adjudicator 1012 sends a request to either the Manufacturer Coupon Administrator 106, or the WHSE Coupon Administrator 107. One of those entities approve the benefit, but instead of providing the benefit on the response, they indicate that it was an approved claim, but the amount paid by the benefit is $0.00 and the consumer's copay remains unchanged. Then, either that entity spins off a transaction to the aggregator who sends a transaction to a bank account, PayPal®, or other merchant services organization and receives approval for payment of the benefit amount that the manufacturer or WHSE wishes to be applied or one of 103, 102, 1012 identifies the approved response with no payment applied and spins off a payment request transaction to PayPal® or merchant services organization to receive payment. The response from the merchant service organization is applied similar to the consumer's payment and is applied to the final aggregated response. Then the Pharmacy Computer 101 receives the payments from a combination of adjudicated responses from the various administrators and the merchant service organization or the benefits aggregator on the behalf of the merchant service organization or manufacturer/WHSE. The manufacturer/WHSE would fund the banking account or merchant service account with the funds needed to pay the benefit.

FIGS. 6A-6B and 7A-7B differ in the sequence of events prior to the inquiry or claim request being forwarded by the Prescription Benefits Adjudicator 1012 to either the or the Prescription Discount Administrator 1011 or the Prescription Benefits Administrator 105. In particular, FIGS. 6A-6B and 7A-7B refer to the situation in which the individual prescription consumer presents a prescription order, whether new or refill, to the dispensing entity, whether pharmacy, dispensing prescriber, or entity acting on behalf of the pharmacy or dispensing prescriber.

FIGS. 8A-8B and 9A-9B illustrate example embodiments in which a prescription consumer 100 with insurance coverage, either him/herself or an entity acting on the prescription consumer's behalf such as an electronic prescription communication service submits an inquiry to a consumer marketplace 108 requesting information about any participating HCP with a Prescription Benefits Administrator 105 that may be able and willing to fulfil the prescription order. Such information may include, but is not limited to, the location of the HCP, the final cost to the prescription consumer for the prescription product, the means of delivery (local pick up, home delivery, mail delivery), the time of delivery, and the ability to pay the final amount due utilizing the prescription consumer's funds processor such as PayPal™, a credit card, a debit card, Health Savings Account, e-check, or other electronic means of payment. The consumer marketplace may provide the consumer the ability to create a secure login associated with a user profile that allows the consumer to store information and preferences which may include but are not limited to: shipping address; physical address; billing address; payment devices; credit card information; debit card information; health savings account information; delivery preferences; default dispensing pharmacy or prescriber location; Prescription list of one or more prescriptions. The prescription list may include, for example, pharmacy identification number; prescription identification number; dispensing pharmacy or prescriber identification number; product information number or other identifying mark; quantity; prescriber identifier; refills remaining; original refills; and expiration date.

The consumer marketplace 108 provides the prescription consumer 100 or other entity acting on the prescription consumer's behalf, such as a prescriber or his agent, with one or more options, if available, for the prescription consumer to select from, in order to facilitate the fulfillment of the prescription order, the collection of the final payment due, and the means by which the prescription consumer wishes to obtain the fulfilled prescription order. Once the prescription consumer selects the location that will fulfill the order, the consumer marketplace forwards to the location the information necessary to fulfill the prescription order whether it be an electronic prescription order from the prescriber or his agent, an electronic image of the prescription order, or the information necessary to obtain the prescription record from a different pharmacy or dispensing prescriber or electronically maintained prescription or medical record housed within the consumer marketplace, an entity acting on behalf of the consumer marketplace, a partner of the consumer marketplace, or an outside entity providing such services.

Once the complete prescription order is obtained by the pharmacy or dispensing prescriber to be fulfilled, steps 10 through 25 proceed to occur. Each step represents an action performed at that location and the submission of the claim to the next entity in the continuum to the end of the description. If any of the steps fail to result in an approved response or completed action, the other steps in the continuum may either continue or the process may be reversed to the beginning with a message being provided to the HCP to make corrections to the submission request or for provision to the prescription consumer as to why the prescription benefit claim request was not successful; one example is as follows: (a) steps 1 through 11 are successful; (b) step 12 fails due to the prescription consumer's insurance benefit being expired; and (c) step 11 is reversed. One or more of consumer marketplace computer 108, the Prescription Consumer 100, and the prescriber computer 109 is provided with a message advising the prescription consumer of the unavailability of prescription benefits due to expired coverage.

FIGS. 10A-10B, 11A-11B, and 12A-12B illustrate example embodiments in which a prescription consumer without insurance coverage, either him/herself or an entity acting on the prescription consumer's behalf such as an electronic prescription communication service submits an inquiry to a consumer marketplace requesting information about any participating HCP that may be able and willing to fulfil the prescription order. These embodiments differ from embodiments discussed earlier in the fact that the prescription consumer does not have prescription insurance coverage. In these embodiments, the prescription consumer may or may not have access to a prescription discount program that is capable of receiving claim requests and sending claim responses online similar to a health insurance administrator. The order in which the individual administrators receive claim requests from the benefits aggregator may vary as ordered by the benefits aggregator. Each step represents an action performed at that location and the submission of the claim to the next entity in the continuum to the end of the description. If any of the steps fail to result in an approved response or completed action, the other steps in the continuum may either continue or the process may be reversed to the beginning with a message being provided to the HCP to make corrections to the submission request or for provision to the prescription consumer as to why the prescription benefit claim request was not successful.

FIGS. 7A-12B refer to the situation in which either the individual prescription consumer, the prescriber, the consumer marketplace or an entity acting on behalf of any of these, presents a prescription order, whether new or refill, to the dispensing entity, whether pharmacy, dispensing prescriber, or entity acting on behalf of the pharmacy or dispensing prescriber.

Other than the interchange of the Prescription Benefits Administrator 105 with the Prescription Discount Administrator 1011, the sequence in which the administrators receive inquiry or claim requests, and how the Pharmacy Computer 101 receives the information to fulfill the prescription order, all steps after that event remain the same. The difference in events prior to that event are determined based on the origin of the inquiry or claim request being the prescription consumer, the consumer marketplace, or the prescriber and the type of request being a new prescription or a refill request. The differences in these details are described in more depth below.

Figure 13:
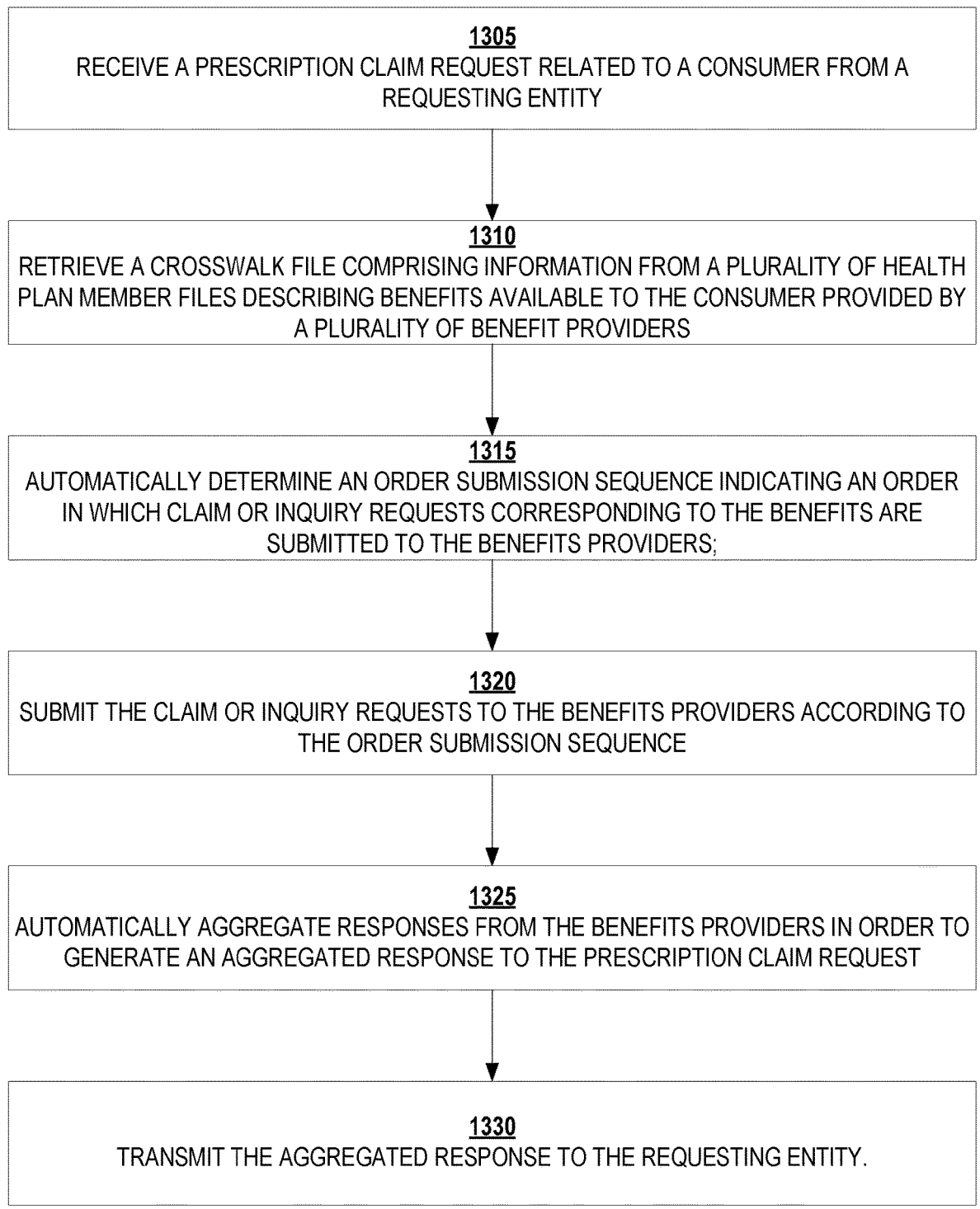
FIG. 13 provides a flowchart depicting a computer-implemented method for managing prescription benefits in prescription claim or inquiry requests performed by one or more computers in a prescription order processing system.

FIG. 13 provides a flowchart depicting a computer-implemented method for managing prescription benefits in prescription claim or inquiry requests performed by one or more computers in a prescription order processing system (see FIG. 1). Starting a step 1305, one of the computers in system receives a prescription claim request related to a consumer from a requesting entity. The prescription claim request may include, for example, an identification of the consumer, a product for which a prescription order or inquiry is being made, the prescriber who created the prescription order for the consumer, and an indication of a dispensing entity which will provide the prescription order to the consumer.

At step 1310, a crosswalk file is retrieved that includes information from a plurality of health plan member files describing benefits available to the consumer provided by a plurality of benefit providers. At step 1315, one of the computers automatically determines an order submission sequence indicating an order in which claim or inquiry requests corresponding to the benefits are submitted to the benefit providers. Various techniques may be used to select the order submission sequence. For example, in some embodiments, the order submission sequence is predetermined and stored in the crosswalk file or another data source. In other embodiments, the order submission sequence is selected by evaluating a plurality of possible order submission sequences according to one or more selection criteria. These selection criteria may be, for example reducing costs to the consumer related to fulfillment of the order or the consumer's preference for certain benefit providers. Where the order submission sequence is determined upon request, various algorithms for optimal ordering generally known in the art may be used. For example, in one embodiment, the order submission sequence is selected using a graph search of possible order submission sequences performed using a graph where each benefit is represented as a node. In other embodiments, the order submission sequence is selected using a tree search of possible submission sequences performed using a graph where each benefit is represented as a node.

Once the order submission sequence is determined the computers then submit the claim or inquiry requests to the benefit providers at step 1320 according to the order submission sequence. At step 1325, one or more of the computers automatically aggregate responses from the benefit providers in order to generate an aggregated response to the prescription claim request. Finally, once the responses are aggregated, the aggregated response is provided to the requesting entity at step 1330. The aggregated response may be in the form of a claim detail file that includes the responses from each claim request that was submitted by the intermediary or benefits aggregator on behalf of the original submitter to the various benefits administrators that were involved in processing benefit claims related to the initial benefit claim request; such file will enable the original submitter to create account receivable records that will enable reconciliation of the payments and the associated payment record detail, whether in electronic report, paper, or standardized format, such as American National Standards Institute (ANSI) Accredited Standards Committee (ASC) X12 form 835, that will be received that are related to the initial claim request.

In some embodiments, data provided on payment request may be aggregated into final claim response processing and provision of some or all funds to original submitter of claim request, for example the Pharmacy Computer 101. Additionally, one or more computers may be used for the creation, formatting and submission of one or more subsequent payment request(s) that may have a different claim format and be sent to other benefit administration types, such as a merchant service organization like MasterCard, Visa, PayPal, American Express, or other financial payment process.

Various configurations of the computers shown in FIG. 1 may be used to one or more of the steps shown in FIG. 13 alone or in combination with other computers. For example, in one embodiment, the Benefits Aggregator 103 performs one or more of the automatic determination of the order submission sequence, the submission of the claim or inquiry requests, and the automatic aggregation of responses from the benefit providers. In other embodiments, the Network Switch Computer 1012 performs one or more of the automatic determination of the order submission sequence, the submission of the claim or inquiry requests, and the automatic aggregation of responses from the benefit providers.

In each of the embodiments discussed herein, the order in which the individual administrators receive benefit claims requests may vary and is defined on a case by case basis by the benefits aggregator. The identification of the available benefits administrators and the order submission sequence in which they are to receive inquiries or claim requests is determined by the data populated in the member ID file database or other file provided by the Benefits Aggregator to an intermediary such as the Network Switch Computer 102 or the Prescription Benefits Adjudicator 1012.

This invention was conceived in the consideration of the above described needs in the marketplace and seeks to address multiple aspects of the needs described. In doing so, there are other issues that can be addressed by default just because the invention exists, such as applying manufacturer-sponsored price discounts, known commonly as rebates, to the appropriate benefit provider s (BP) and causing those discounts to flow through that BP to the individual consumer based on the benefit design in which the individual consumer has chosen to participate. It should be understood that someone skilled in the art of healthcare benefits provision, healthcare claims flow, and the data included in healthcare claims could extrapolate the functionality of this invention to relate to other problems in the financial claims billing process for healthcare claims. It should also be understood that someone skilled in the art of healthcare benefits provision, healthcare claims flow and the data included in healthcare claims could understand that a prescription adjudication software or other computerized entity could be enabled in such a way as to replace one or more of the network switch computer(s) or one or more of the administrator computers for one or multiple of the actions the attached or other embodiments describe. It should also be understood that someone skilled in the art of healthcare benefits provision, healthcare claims flow and the data included in healthcare claims, could understand that one or more network switches could be enabled in such a way as to replace one or more of the administrators for one or multiple of the actions the attached or other embodiments described herein.

Various entities may leverage the capabilities of the benefits aggregator. For example, the benefits aggregator may be engaged by an insurance provider to apply pharmaceutical discounts or rebates to claims for insurance benefits to the amount billed to the insurance provider prior to the claim arriving to the insurance provider for payment consideration. A pharmaceutical company may engage the benefits aggregator to provide discounts or rebates to the consumer, whether the individual or the insurer, prior to or after the insurance provider receives a claim for payment consideration in order to provide cost savings to the purchaser of the product according to the benefit design provided to the individual by the insurer. A submitter (e.g., a pharmacy or prescriber location) may use the benefits aggregator to do one or more of the following: re-calculate; redirect; create; submit; and/or aggregate claim or inquiry requests and claim or inquiry responses in the proper sequence and in the proper format, whether one-to-many or many-to-one on their behalf to and from the various benefit providers that have engaged the benefits aggregator for its claim aggregation and prioritization services. Finally, an individual consumer may engage the benefits aggregator to submit benefit requests or inquiries on his or her behalf to the various benefit providers, irrespective to the individual's awareness of the availability of benefits.

In these embodiments, there are several actions that may occur by the various entities discussed herein. For example, in one embodiment, an action is taken by the network switch, the benefits aggregator, or other entity with the ability to intercept prescription benefit claim requests and responses that are addressed to be sent to a specific administration location or returned to a specific HCP location including identifying specific claim attributes that pertain to a set of rules and data elements provided to separate a specific claim request or response from others that may be similar. These may include, for example identifying the claim request that is submitted by the prescriber, the individual consumer or the submitter (usually a pharmacy or prescriber location) or returning as a claim or inquiry response from a benefits administrator as having potential for additional benefits by matching the information that is contained in the claim transmission data to a database of information obtained from the insurance provider, the rebate or discount provider, the individual consumer, the benefits aggregator, the submitter (usually a pharmacy or prescriber location), or the network switch. The information that is matched may include, for example, claim transaction identification; claim origin or submitter identification number; Rx number; refill number; product identification; quantity submitted; banking identification number; processor control number; group number; member identification number; person code; dependent code; date of birth; gender code.

Another action that may be performed is re-formatting and populating the claim request with alternate information that directs it to one or more benefits administrators for consideration for benefits, populates the claim in such a way as to appear that other benefits have been provided already. For example, the claim request can be sent to a "rebate administrator" for consideration and application of the rebate benefit to lower the financial amount due for consideration by subsequent benefit providers. Alternatively, the data can be managed internally in such a manner as to reflect the actions that would be taken by an external "rebate administrator" such as: applying contractual discounts between the insurance provider and the submitter (usually a pharmacy or prescriber location) similar in nature to the discount rate applied by a Prescription Benefit Manager on behalf of the insurance provider, and/or applying rebates or discounted amounts provided by the pharmaceutical manufacturer or distributor that are associated with the product being provided with or without relation to the quantity or amount of the product being provided.

Another action that may be performed by the entities discussed herein is generating, storing, accumulating, and aggregating the claim or inquiry responses from one or more claim requests or inquiries that were submitted on behalf of the individual consumer and/or the submitter (usually a pharmacy or prescriber location) to various benefit administrators utilizing the proper format for each request, possibly, but not necessarily using data contained in one or more responses from previous benefits administrators.

Various other actions may be performed in addition to, or as an alternative to the actions discussed above. For example, in some embodiments, the action includes receiving, storing, accumulating, and aggregating the responses from one or more previous benefits administrators or calculations. In other embodiments, the action includes formatting the final claim response to the submitter (usually a pharmacy or prescriber location) into a single, aggregated claim or inquiry response that provides the aggregate effect of all benefits provided on all applicable claim inquiry responses or calculations. In other embodiments, the actions include ceasing the process, submitting reversal claims or inquiries and accepting reversal responses to all related successful claims or inquiries if one or more of the related claims or inquiries are rejected or denied by the benefit providers if such action is necessary. In other embodiments, the action includes notifying the submitter (usually a pharmacy or prescriber location) or the individual consumer of the reason(s) one or more of the claim(s) or inquiry (ies) were denied or rejected if such action is necessary. In other embodiments, the actions include providing individual claim responses that made up the aggregated response to some type of business or service that provides claim payment reconciliation services on the behalf of the dispenser of the prescription product, whether the prescriber, the pharmacy, or other entity, or to the individual consumer for identification of the amount of benefits provided and the identity of the benefit providers that may have provided all or part of the aggregated benefit. In other embodiments, the actions include providing paper, electronic report, or other electronically formatted file detailing the payment amount that was sent either from the BP or on the behalf of the BP to the dispensing prescriber, pharmacy, or other entity in order to facilitate reconciliation of the payment received with the individual amounts that made up the aggregated response on the final, approved claim response.

Each of the above tasks may be performed by a computerized system with the hardware and software capability of processing and/or redirecting prescription claims in a rapid fashion anywhere in the electronic network between when the claim data leaves the data entry point (usually a pharmacy or prescriber location) and when the final claim response arrives back at the point of origin (usually the submitting pharmacy or prescriber location). These actions, acting in concert with each other or, in some cases, alone, provide a unique capability that will greatly assist in the proper application of the various benefits that are available to prescription consumers in order to lower total costs for prescription products throughout the marketplace.

In each of the embodiments, the order in which the individual administrators receive benefit claims requests may vary and is defined on a case by case basis by the benefits aggregator. The identification of the available benefits administrators and the order sequence in which they are to receive inquiries or claim requests is determined by the data populated in the UPI member crosswalk (see FIG. 3) or other file provided by the benefits aggregator to an intermediary such as the Network Switch Computer 102 or the Prescription Benefits Adjudicator 1012.

It should be understood that there are many other embodiments, both shown in drawings and not displayed at all that could be learned from experiencing the possibilities and capabilities of this invention. The limited details and embodiments described herein should not be interpreted as to limit the scope or future embodiments that may pertain to this invention.

It should be noted that the present invention does not rely on the pharmacy to be aware of, identify or submit the information necessary for any subsequent claim to be submitted. The techniques described herein do not rely on information contained in the transaction to determine either what benefit requests are to be submitted or the sequence in which they are to be submitted. It is similar in that the network switch or another computer entity will aggregate the financials from the claim responses and submit back to the pharmacy, but also different in the fact that the network switch or other computer entity may send back to the pharmacy a data file that contains each response that occurred in relation to the original benefit claim request for the pharmacy to use for reconciliation purposes.

FIG. 14 illustrates an exemplary computing environment 1400 within which embodiments of the invention may be implemented. For example, the computing environment 1400 may be used to implement any of the computers illustrated in FIG. 1. The computing environment 1400 may include computer system 1410, which is one example of a computing system upon which embodiments of the invention may be implemented. Computers and computing environments, such as computer system 1410 and computing environment 1400, are known to those of skill in the art and thus are described briefly here.

As shown in FIG. 14, the computer system 1410 may include a communication mechanism such as a bus 1421 or other communication mechanism for communicating information within the computer system 1410. The computer system 1410 further includes one or more processors 1420 coupled with the bus 1421 for processing the information. The processors 1420 may include one or more central processing units (CPUs), graphical processing units (GPUs), or any other processor known in the art. In some embodiments, a cloud-based computing environment may be used for implementing the systems and methods described herein. Techniques such as server virtualization can be used to maximize the use of hardware resources.

The computer system 1410 also includes a system memory 1430 coupled to the bus 1421 for storing information and instructions to be executed by processors 1420. The system memory 1430 may include computer readable storage media in the form of volatile and/or nonvolatile memory, such as read only memory (ROM) 1431 and/or random access memory (RAM) 1432. The system memory RAM 1432 may include other dynamic storage device(s) (e.g., dynamic RAM, static RAM, and synchronous DRAM). The system memory ROM 1431 may include other static storage device(s) (e.g., programmable ROM, erasable PROM, and electrically erasable PROM). In addition, the system memory 1430 may be used for storing temporary variables or other intermediate information during the execution of instructions by the processors 1420. A basic input/output system (BIOS) 1433 containing the basic routines that help to transfer information between elements within computer system 1410, such as during start-up, may be stored in ROM 1431. RAM 1432 may contain data and/or program modules that are immediately accessible to and/or presently being operated on by the processors 1420. System memory 1430 may additionally include, for example, operating system 1434, application programs 1435, other program modules 1436 and program data 1437.

The computer system 1410 also includes a disk controller 1440 coupled to the bus 1421 to control one or more storage devices for storing information and instructions, such as a hard disk 1441 and a removable media drive 1442 (e.g., floppy disk drive, compact disc drive, tape drive, and/or solid state drive). The storage devices may be added to the computer system 1410 using an appropriate device interface (e.g., a small computer system interface (SCSI), integrated device electronics (IDE), Universal Serial Bus (USB), or FireWire).

The computer system 1410 may also include a display controller 1465 coupled to the bus 1421 to control a display 1466, such as a liquid crystal display (LCD) or light emitting diode (LED) monitor, for displaying information to a computer user. The computer system includes an input interface 1460 and one or more input devices, such as a keyboard 1462 and a pointing device 1461, for interacting with a computer user and providing information to the processors 1420. The pointing device 1461, for example, may be a mouse, a trackball, or a pointing stick for communicating direction information and command selections to the processors 1420 and for controlling cursor movement on the display 1466. The display 1466 may provide a touch screen interface which allows input to supplement or replace the communication of direction information and command selections by the pointing device 1461.

The computer system 1410 may perform a portion or all of the processing steps of embodiments of the invention in response to the processors 1420 executing one or more sequences of one or more instructions contained in a memory, such as the system memory 1430. Such instructions may be read into the system memory 1430 from another computer readable medium, such as a hard disk 1441 or a removable media drive 1442. The hard disk 1441 may contain one or more datastores and data files used by embodiments of the present invention. Datastore contents and data files may be encrypted to improve security. The processors 1420 may also be employed in a multi-processing arrangement to execute the one or more sequences of instructions contained in system memory 1430. In alternative embodiments, hard-wired circuitry may be used in place of or in combination with software instructions. Thus, embodiments are not limited to any specific combination of hardware circuitry and software.

As stated above, the computer system 1410 may include at least one computer readable medium or memory for holding instructions programmed according to embodiments of the invention and for containing data structures, tables, records, or other data described herein. The term "computer readable medium" as used herein refers to any medium that participates in providing instructions to the processor 1420 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 1441 or removable media drive 1442. Non-limiting examples of volatile media include dynamic memory, such as system memory 1430. Non-limiting examples of transmission media include coaxial cables, copper wire, and fiber optics, including the wires that make up the bus 1421. Transmission media may also take the form of acoustic or light waves, such as those generated during radio wave and infrared data communications.

The computing environment 1400 may further include the computer system 1410 operating in a networked environment using logical connections to one or more remote computers, such as remote computer 1480. Remote computer 1480 may be a personal computer (laptop or desktop), a mobile device, a server, a router, a network PC, a peer device or other common network node, and typically includes many or all of the elements described above relative to computer system 1410. When used in a networked environment, computer system 1410 may include modem 1472 for establishing communications over a network 1471, such as the Internet. Modem 1472 may be connected to bus 1421 via user network interface 1470, or via another appropriate mechanism.

Network 1471 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 1410 and other computers (e.g., remote computer 1480). The network 1471 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 1471.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112(f), unless the element is expressly recited using the phrase "means for."

We claim:

1. A method for prescription benefits, comprising the steps:

receiving a prescription claim request related to a consumer from a requesting entity, wherein said consumer has a consumer profile (100), wherein said requesting entity is a network switch computer (102), wherein a prescription claim request is comprised of one of a group consisting of a rebate claim request, a manufacturer coupon claim request, and a wholesale coupon claim request, and wherein the step of receiving said prescription claim request is comprised of the steps of:

A. sending claim targeting information from a benefit aggregator (103) to said network switch computer (102), said benefit aggregator being in communication with said network switch computer;

B. sending rebate plan setup information from said benefit aggregator to a rebate administrator (104);

C. sending manufacturer coupon plan setup information from said benefit aggregator to a manufacturer coupon administrator (106);

D. sending wholesale coupon plan setup information from said benefit aggregator to a wholesale coupon administrator (107) so as to form a crosswalk file comprised of said claim targeting information, said rebate plan setup information, said manufacturer coupon plan setup information, and said wholesale coupon plan setup information as information from a plurality of health plan member files describing benefits available to the consumer provided by a plurality of benefit providers, wherein the rebate administrator, the manufacturer coupon administrator, and the wholesale coupon administrator are benefit providers;

E. setting up said consumer (100) profile in a consumer marketplace (108);

F. sending a purchase information for prescription product inquiry from said consumer to the consumer marketplace (108) so as to receive a purchase information for prescription product response;

G. sending said purchase information for prescription product response from the consumer marketplace to said consumer;

H. sending a prescription according to said purchase information for prescription product response from said consumer to a pharmacy computer (101);

I1. sending a consumer prescription claim request according to said prescription from said pharmacy computer to said network switch computer (102), the consumer marketplace and said pharmacy computer being in communication with the rebate administrator through said benefit aggregator and said network switch computer, the consumer marketplace and said pharmacy computer being in communication with the prescription benefits administrator, the manufacturer coupon administrator, and the wholesale coupon administrator through said network switch computer;

I2. retrieving said crosswalk file;

I3. using said crosswalk file to automatically determine an order submission sequence indicating an order in which said rebate claim request, said manufacturer coupon claim request, and said wholesale coupon claim request are submitted to corresponding benefit providers;

I4. submitting said rebate claim request, said manufacturer coupon claim request, and said wholesale coupon claim request to the corresponding benefit providers according to said order submission sequence, wherein the step of submitting according to said order submission sequence is comprised of the steps of:

J. identifying a rebate plan claim and a rebate claim price according to said rebate plan setup information with said network switch computer;

K. formatting said rebate plan claim request according to said rebate plan setup information with said network switch computer;

L. sending said rebate plan claim, said rebate claim price, and said rebate plan claim request to the rebate plan administrator (104) from said network switch computer (102) so as to receive a rebate plan response, according to said rebate plan setup information, wherein a prescription benefits administrator having prescription benefits set up information is in communication with said network switch computer;

M. identifying a prescription benefits claim and a prescription benefits claim price according to said prescription benefits plan setup information and said rebate plan response with said network switch computer;

N. formatting a prescription benefits request according to said prescription benefits plan setup information and said rebate plan response with said network switch computer;

O. sending the prescription benefits request to said prescription benefits administrator (105) from said network switch computer (102) so as to receive a prescription benefits response, according to said prescription benefits plan setup information and said rebate plan response;

P. identifying a manufacturer coupon claim and a manufacturer coupon claim price according to said manufacturer coupon plan setup information, said rebate plan response, and said prescription benefits response with said network switch computer;

Q. formatting the manufacturer coupon request according to said manufacturer coupon plan setup information, said rebate plan response, and said prescription benefits response with said network switch computer;

R. sending the manufacturer coupon request to the manufacturer coupon administrator (106) from said network switch computer (102) so as to receive a manufacturer coupon response, according to said manufacturer coupon plan setup information, said rebate plan response, and said prescription benefits response;

S. identifying a wholesale coupon claim and a wholesale coupon claim price according to said wholesale coupon plan setup information, said rebate plan response, said prescription benefits response, and said manufacturer coupon response with said network switch computer;

T. formatting a wholesale coupon request according to said wholesale coupon plan setup information, said rebate plan response, said prescription benefits response and said manufacturer coupon response with said network switch computer;

U. sending the wholesale coupon request to the wholesale coupon administrator (107) from said network switch computer (102) so as to receive a wholesale coupon response, according to said manufacturer coupon plan setup information, said rebate plan response, said prescription benefits response, and said manufacturer coupon response;

automatically aggregating said rebate plan response, said prescription benefits response, said manufacturer coupon response, and said wholesale coupon response in order to generate an aggregated response to said consumer prescription claim request, wherein the step of automatically aggregating comprises the steps of:

V. sending a final payment request, according to said rebate plan response, said prescription benefits response, said manufacturer coupon response, and said wholesale coupon response, with said network switch computer to the consumer marketplace (108), wherein said aggregated response is further comprised of one of a group consisting of said purchase information for prescription product response and said final payment request;

W. sending a consumer confirmation, according to said final payment request from said consumer through the consumer marketplace;

X. sending a rebate plan confirmation, a prescription benefits confirmation, a manufacturer coupon confirmation, and a wholesale coupon confirmation, to said benefits aggregator (103) from said network switch computer according to said consumer confirmation so as to form said aggregated response; and transmitting said aggregated response said pharmacy computer, wherein the step of transmitting said aggregated response comprises the step of:

Y. sending said aggregated response to said pharmacy computer at a pharmacy; and Z. delivering a prescription product to said consumer at said pharmacy in exchange for a final payment according to said final payment request and said aggregated response.

2. The method for prescription benefits, according to claim 1, wherein the step of G. sending said purchase information for prescription product inquiry comprises the steps of:

G1. sending said purchase information for prescription product inquiry from the consumer marketplace (108) to said benefit aggregator (103); and G2. sending said purchase information for prescription product response to the consumer marketplace (108) from said benefit aggregator (103).

3. The method for prescription benefits, according to claim 1, wherein the step of R. sending the manufacturer coupon request to the manufacturer coupon administrator (106) from said network switch computer (102) comprises the steps of:

R1. requesting approval from an eligible inventory administrator based on quantity with the manufacturer coupon administrator, said eligible inventory administrator being in communication with said manufacturer coupon administrator; and R2. receiving an eligible inventory response from said eligible inventory administrator so as to determine said manufacturer coupon response.

4. The method for prescription benefits, according to claim 1, wherein the step of U. sending the wholesale coupon request to the wholesale coupon administrator (107) from said network switch computer (102) comprises the steps of:

U1. requesting approval from said an eligible inventory administrator based on quantity with the wholesale coupon administrator, said eligible inventory administrator being in communication with said wholesale coupon administrator; and U2. receiving an additional eligible inventory response from the eligible inventory administrator so as to determine said wholesale coupon response.

5. The method for prescription benefits, according to claim 1, wherein said consumer prescription claim request comprises:

an identification of said consumer, a product for a prescription order, and a prescriber associated with said consumer.

6. The method for prescription benefits, according to claim 5, wherein said consumer prescription claim request further comprises:

an indication of a dispensing entity for said product.

* * * * *